US010119850B2

(12) United States Patent
Mohr et al.

(10) Patent No.: US 10,119,850 B2
(45) Date of Patent: *Nov. 6, 2018

(54) APPARATUS FOR IDENTIFYING AND MEASURING VOLUME FRACTION CONSTITUENTS OF A FLUID

(71) Applicant: Mohr and Associates, Richland, WA (US)

(72) Inventors: Charles L. Mohr, Richland, WA (US); Brandt C. Mohr, Richland, WA (US); Benno Mohr, Pullman, WA (US); Michael Stordahl, Kennewick, WA (US); James Van Corbach, Sunnyside, WA (US); Erik Von Reis, Kennewick, WA (US); Christopher Mulkey, West Richland, WA (US); Ryan Sams, Kennewick, WA (US); David Hurley, Pasco, WA (US); Gordon Anderson, Benton City, WA (US); Daniel Kenney, Richland, WA (US); William Rausch, Richland, WA (US); Edgar Gilbert, Ocean Shores, WA (US)

(73) Assignee: Mohr and Associates, Richland, WA (US)

( * ) Notice: Subject to any disclaimer, the term of this patent is extended or adjusted under 35 U.S.C. 154(b) by 257 days.

This patent is subject to a terminal disclaimer.

(21) Appl. No.: 15/172,558

(22) Filed: Jun. 3, 2016

(65) Prior Publication Data

US 2017/0350740 A1 Dec. 7, 2017

(51) Int. Cl.
*G01F 1/74* (2006.01)
*G01F 1/708* (2006.01)
*G01F 5/00* (2006.01)

(52) U.S. Cl.
CPC ............... *G01F 1/74* (2013.01); *G01F 1/708* (2013.01); *G01F 5/00* (2013.01)

(58) Field of Classification Search
CPC ............... G01F 1/74; G01F 1/708; G01F 5/00
USPC ........................................... 73/61.44
See application file for complete search history.

(56) References Cited

U.S. PATENT DOCUMENTS

| 4,760,742 A | 8/1988 | Hatton |
| 4,786,857 A | 11/1988 | Mohr et al. |
| 5,095,758 A | 3/1992 | Cox et al. |
| 5,127,272 A | 7/1992 | Dean et al. |
| 5,249,455 A | 10/1993 | Cox |
| 5,259,239 A | 11/1993 | Gaisford |
| 5,272,444 A | 12/1993 | Cox |
| 5,551,305 A | 9/1996 | Farchi et al. |
| 5,723,979 A | 3/1998 | Mohr |
| 6,144,211 A | 11/2000 | Mohr |

(Continued)

OTHER PUBLICATIONS

Notification of Transmittal of the International Search Report and the Written Opinion of the International Searching Authority or the Declaration, dated Jul. 19, 2017.

*Primary Examiner* — Hezron E Williams
*Assistant Examiner* — Marrit Eyassu
(74) *Attorney, Agent, or Firm* — Randall Danskin P.S.

(57) ABSTRACT

An apparatus for identifying and measuring volume fraction constituents of a fluid using time domain analysis and frequency domain analysis to identify individual volume fraction constituents within a pipe on a real time basis and to measure the volume of the individual volume fraction constituents flowing through the pipe on a real time basis.

8 Claims, 21 Drawing Sheets

(56) References Cited

U.S. PATENT DOCUMENTS

| | | |
|---|---|---|
| 6,348,803 B1 | 2/2002 | Mohr |
| 2004/0000203 A1* | 1/2004 | Brandhorst .......... A61C 9/0026 73/866 |
| 2006/0081066 A1* | 4/2006 | Drobyshev ........... G01F 1/7088 73/861.04 |
| 2009/0126502 A1* | 5/2009 | Wee ..................... G01F 1/44 73/861.04 |
| 2010/0145636 A1 | 6/2010 | Nyfors |
| 2012/0014405 A1 | 1/2012 | Anderson et al. |
| 2013/0345994 A1* | 12/2013 | Wiklund ................ G01F 1/34 702/46 |
| 2014/0299210 A1* | 10/2014 | Atherton ................ G01F 1/74 137/624.27 |
| 2014/0358447 A1* | 12/2014 | Doyle ................... A61B 8/085 702/19 |

* cited by examiner

APPARATUS FOR IDENTIFYING AND MEASURING VOLUME FRACTION CONSTITUENTS OF A FLUID

TECHNICAL FIELD

This invention relates to an apparatus for identifying and determining relative proportions of intermixed volume fraction constituents of a fluid using reflected electrical signals and resonance points.

BACKGROUND OF THE INVENTION

The current practice in the oil and gas and petroleum chemical/fuel industry for identifying measuring quantities of oil, water, natural gas and other components being produced by a given well, or group of wells, to separate the produced components in a separator and to identify and measure the produced components individually. The separators are typically large, expensive, maintenance intensive and typically provide production information only after long intervals during which the components separate under the influence of gravity.

Similarly, when a well is being drilled, drilling fluids ("drilling mud"), which one typically complex mixtures of synthetic and organic compounds which are expensive and proprietary in nature, are regurgitated from the wellbore being drilled. The drilling mud is used to lubricate the cutter head, and also to evacuate "cuttings" and rock chips and the like from the wellbore. Further, the drilling mud seals and stabilizes the circumferential walls of the wellbore to prevent leakage, collapse and the like. The fluids which are regurgitated from the wellbore are typically transferred to a settling pond for the solids to "settle out" and thereafter the fluids are transferred to a separator to identify and measure the individual components which may thereafter be reused in the drilling process.

To address the drawbacks of separators, composition meters have been developed to continuously measure volume fractions of natural gas, water and oil being produced. When such a composition meter is combined with a flow meter, production rates for the various components may also be calculated. Known composition meters use measurement of dielectric constant, in combination with a density measurement, to determine the volume fractions.

For known composition meters to be consistently accurate, all the dielectric constants and all the densities of the individual produced fluid components must be known for every measurement condition (temperature and pressure). Unfortunately, this is nearly impossible to accomplish because all the conditions are continually varying and changing as the well is drilled and as the oil well, or group of oil wells, produce. Accuracy of the measurements is further complicated by several of the lower density hydrocarbon components (for example but not limited to, ethane, propane, butane and pentane) existing in either a liquid state or a gaseous state at pressures between approximately 20 and 250 atmospheres. Further, the produced components are typically at very high temperatures and as a result, produced water boils off into steam within the pipes causing identification and measurements of gaseous components to be particularly difficult because the dielectric constant of steam is very close to the dielectric constants of the lower density hydrocarbon components.

Prior art publications claim it is "impossible" to accurately identify and measure the volume fractions of oil, water, and natural gas without knowing how much of each hydrocarbon constituent is in the liquid or gaseous phase at any given time.

Another important measurement problem in the oil and hydrocarbon production industry is the accurate measurement of water content. Water content directly affects the price paid for the product. Various devices are available to continuously measure water content, and most such devices are capacitance meters which measure the dielectric constant of the oil/water mixture to determine the water content. Unfortunately, such devices, which are known in the industry as "water cut meters" are not continuously accurate because the temperature, density and dielectric constant of the oil/water mixture ail change as measurement conditions change, which results in measurement errors.

A further complicating factor in measuring volume fraction constituents of mixtures of produced oil and water and natural gas is the salt content of the mixture. The salt also affects the dielectric constant of the fluid components. Similarly, lubricants within the drilling mud and proprietary lubricating drilling fluids may further affect the dielectric constants of the components which may make accurate identification and measurements difficult.

Our apparatus for identifying and measuring volume fraction constituents of a fluid overcomes various of the drawbacks of known volume fraction constituent identifying and measuring apparatus.

SUMMARY OF THE INVENTION

A first aspect of the present invention is an apparatus for identifying and measuring volume fraction constituents of a fluid, comprising a source of fluid with a known temperature, and having a volume fraction constituent, and wherein the volume fraction constituent has a previously calculated and known dielectric constant and a previously calculated and known resonance points, and wherein information about the previously calculated, and known dielectric constant and resonance points is stored in and is accessible from a database; a probe exposed, at least in part, to the fluid, and wherein the probe has a known length; an electrical pulse emitter which electronically generates a electrical pulse which is delivered to the probe, and which travels the known length of the probe and which generates an electrical pulse reflection; an electrical pulse sampler which electronically communicates with the probe and which further receives and senses the electrical pulse reflection generated by electrical pulse within the probe; a computer electronically coupled with the probe, the electrical pulse emitter, the electrical pulse sampler, and the database, and wherein the computer determines a time period between the electrical pulse emission into the probe and the receipt of the sensed electrical pulse reflection, and wherein the resonance points of the volume fraction constituent is calculated by the computer from the time period which is determined, and wherein the computer further correlates the determined time period to the previously calculated, and known dielectric constant and previously calculated and known resonance points of the volume fraction constituent as provided in the database so as to identify the volume fraction constituent in the fluid and determine a volume of the volume fraction constituent in the fluid; and a user interface electronically coupled with the computer, and which further generates a user perceivable output which identifies the volume fraction constituent of the volume of the volume fraction constituent.

A second aspect of the present invention is wherein the volume fraction constituent is selected from the group consisting of petroleum, water, natural gas and drilling fluid.

A third aspect of the present invention is wherein the volume fraction constituent is a multiplicity of volume fraction constituents.

A fourth aspect of the present invention is wherein the multiplicity of volume fraction constituents includes a fluid and a gas.

A fifth aspect of the present invention includes a pipe having a known interior diameter communicating with the source of the fluid so that a volume of the fluid moves through the pipe at a velocity; a second probe exposed at least in part to the fluid moving through the pipe a known distance downstream from the first probe; a first output generated by the first probe when a volume fraction constituent is sensed by the first probe and a second output generated by the second probe when the same volume fraction constituent is subsequently sensed by the second probe, and wherein the first and second probe outputs are communicated to the computer; and the computer uses a time difference between the first probe output and the second probe output to determine the velocity of the fluid moving through the pipe and by correlating the determined velocity with a known volume of fluid moving through the pipe a volume of the volume fraction constituent is determined by the computer and by correlating the resonance points of the volume fraction constituent to the resonance points for various constituents of volume fraction constituents in the fluid, the volume of the volume fraction constituent is determined.

A sixth aspect of the present invention includes a backpressure regulator communicating with the pipe to maintain fluid pressure within the pipe and about the probes at a pressure at least equal to the pressure of the source of the fluid to prevent boiling within the pipe.

A seventh aspect of the present invention is a method for identifying and measuring a volume fraction constituent of a fluid, the method comprising providing a source of fluid, the fluid having a volume fraction constituent, and wherein the volume fraction constituent has a previously calculated and known dielectric constant, and previously calculated and known resonance points; providing a database having accessible stored information about the previously calculated and known dielectric constant of the volume fraction constituent and having accessible and stored information about the previously calculated and known resonance points of the volume fraction constituent; providing a probe exposed, at least in part, to the fluid, and wherein the probe has a known length; providing an electrical pulse emitter which electronically generates an electrical pulse which is delivered to the probe, and which further travels the known length of the probe and which generates an electrical pulse reflection; providing an electrical pulse sampler electronically coupled with the probe and which further receives and senses the electrical pulse reflection generated by electrical pulse within the probe; providing a computer electronically coupled with the probe, the electrical pulse emitter, the electrical pulse sampler and the database, and wherein the computer determines a time period between the electrical pulse emission into the probe, and the receipt of the sensed electrical pulse reflection, and wherein the resonance points of the volume fraction constituent are calculated by the computer from the determined time period, and wherein the computer further correlates the determined time period to the previously calculated and known dielectric constant and the previously calculated and known resonance points of the volume fraction as provided in the database to identify the volume fraction constituent in the fluid; and providing a user interface electronically coupled with the computer, and which further generates a user perceivable output which identifies the volume fraction constituent in the fluid.

An eighth aspect of the present invention includes applying a Fast Fourier Transform (FFT) to the determined time period to determine the resonance points which may be resonance frequencies of the volume fraction constituent.

A ninth aspect of the present invention is wherein the volume fraction constituent is selected from the group consisting of petroleum, water, petroleum, gas and drilling fluids.

A tenth aspect of the present invention is wherein the volume fraction constituent is a multiplicity of volume fraction constituents.

An eleventh aspect of the present invention is wherein the multiplicity of volume fraction constituents includes a liquid and a gas.

A twelfth aspect of the present invention includes providing a pipe having a known interior diameter communicating with the source of a volume of the fluid so that the fluid moves through the pipe at a velocity; providing a second probe exposed at least in part to the fluid moving through the pipe a known distance downstream from the first probe; generating a first output by the first probe when a volume fraction constituent is sensed by the first probe and generating a second output by the second probe when the same volume fraction constituent is subsequently sensed by the second probe, and communicating the first and second probe outputs to the computer; and determining a velocity of each volume fraction constituent moving through the pipe by calculating a time difference between the first probe output and the second probe output and determining the volume of each volume fraction constituent moving through the pipe.

A thirteenth aspect of the present invention includes maintaining fluid pressure about the probes at a pressure at least equal to the pressure of the source of the fluid to prevent boiling within the pipe.

A fourteenth aspect of the present invention includes providing a back pressure regulator communicating with the pipe downstream of the probe.

A fifteenth aspect of the present invention is a method for identifying and measuring a volume fraction constituent of a fluid comprising determining a dielectric constant of a volume fraction constituent by determining a time delay between an electrical pulse emission into a probe exposed, at least in part, to the fluid and a reflection of the electrical pulse from the probe; correlating the determined time delay to a database of known dielectric constants of known volume fraction constituents which generate similar time delays to identify the volume fraction constituent; applying a Fast Fourier Transform to the determined time delay to generate a sine wave frequency of the volume fraction constituent; calculating a power spectral density calculation to determine the power and resonance points of the sine wave frequency; correlating the generated resonance points of the volume fraction constituent to a database of known resonance points of known concentration of volume fraction constituents to identify the volume fraction constituent; and providing a user interface which generates a user perceivable output of the identified and measured volume fraction constituents in the fluid in a user perceivable form.

A sixteenth aspect of the present invention includes providing a pipe having a known interior diameter communicating with the source of the fluid so that a volume of the fluid moves through the pipe at a velocity; providing a second probe exposed at least in part to the fluid moving through the pipe a known distance downstream from the first probe; generating a first output by the first probe when a volume fraction constituent is sensed by the first probe, and generating a second output by the second probe when the same volume fraction constituent is subsequently sensed by the second probe, and communicating the first and second probe outputs to the computer; and determining a velocity of the volume fraction constituent moving through the pipe by calculating a time difference between the first probe output and the second probe output with the known interior diameter of the pipe and known volume of fluid moving through the pipe; and correlating the resonance points of the volume fraction constituent to the resonance points for various concentrations of volume fraction constituents in the fluid the volume of the volume fraction constituent is determined.

A seventeenth aspect of the present invention is a probe formed of Inconel® Alloy having a chrome alumina oxide coating extending entirely thereabout and having an electrical impedance of approximately 90 ohms in air.

BRIEF DESCRIPTION OF THE DRAWINGS

FIG. 6 is an orthographic front view of the probe of FIG. 6 less the support block.

DETAILED DESCRIPTION OF THE PREFERRED EMBODIMENTS

Figure 1:
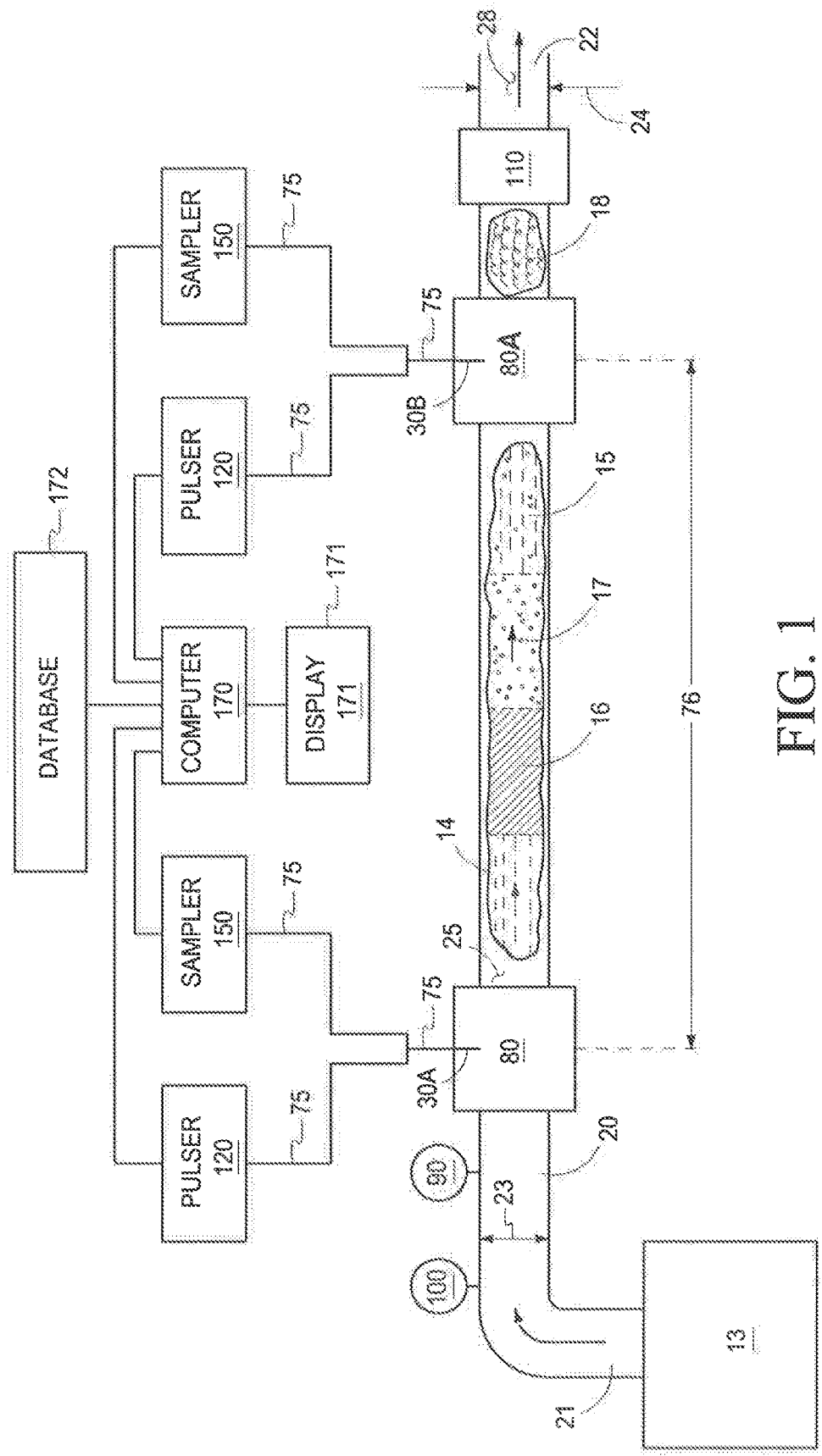
FIG. 1 is a generalized block diagram of our apparatus showing arrangement of the various components and fluid flow therethrough.

This disclosure of the invention is submitted in furtherance of the Constitutional purposes of the U.S. Patent Laws "to promote the progress of science and useful arts" (Article 1, Section 8).

An apparatus for identifying and measuring volume fraction constituents of a fluid generally comprises a source of fluid 13, a pipe 20, a probe 30, a grayloc support 80, a pulse emitter 120, a pulse sampler 150, a computer 170, and a support frame 200.

The source of fluid 13 is typically an oil well, or grouping of oil wells producing a fluid 14 that contains a mixture of various volume fractions including, but not limited to, oil 15, water 16 and natural gas 17. The source of fluid 13 may also be a stream of fluid 14 or a settling pond or similar volume of fluid 14 used in the drilling of a well (not shown) and including without limitation, drilling fluid or "drilling mud". (not shown). It is also contemplated the source of fluid 13 may be a volume of stored fluid 14 such as a volume of fuel within a storage tank (not shown). When produced from the source of fluid 13, the fluid 14 is at pressure and is typically at a temperature that may exceed ambient temperature by hundreds of degrees, although the temperature and pressure vary over time and conditions. It is further contemplated and anticipated the fluid 14 volume fraction constituents 15, 16, 17 may be produced, and flow through the pipe 20, in segregated fashion, and at other times it is anticipated the volume fraction constituents 15, 16, 17 will be a mixture or emulsions 18 of fluid 14 that may or may not be homogeneously distributed within the pipe 20.

Oil 15, water 16 and natural gas 17 are different molecular compounds, and have different, well recognized dielectric constants and resonance points depending upon the concentration. The dielectric constant of water 16 ranges from approximately 80 for cold water down to approximately 25 for very hot water. The dielectric constant of steam is approximately 1.01 increasing to approximately 1.15 as temperature increases. The dielectric constant of oil 15 is approximately 2.0 to 2.5 depending upon the density of the oil 15. The dielectric constant of natural gas 17 is approximately 1.2 to approximately 1.6.

Because the known dielectric constant of steam (approximately 1.01-1.15) is similar to the dielectric constant of natural gas 17 (approximately 1.2-1.6) use of a back pressure regulator 110 communicating with the pipe 20 maintains pressure within the pipe 20 at a pressure at least equal to the pressure of the fluid 14 exiting the source of fluid 13. With the use of a back pressure regulator 110, even though the fluid 14 may be at an extremely high temperature, the water 16 within the fluid 14 will not boil, and will remain in a liquid state with the corresponding dielectric constant and resonance points which are measurably different than the dielectric constant of natural gas 17. Preventing the formation of steam inside the pipe 20 allows the instant apparatus to distinguish between natural gas 17, and water 16 using the known dielectric constants and resonance points thereof.

The pipe 20 has an inflow end 21 communicating with the source of fluid 13 and an outflow end 22 communicating with a distribution point (not shown) such as a collection facility (not shown). The pipe 20 has a known interior diameter 23, an exterior diameter 24, an exterior surface 25, defines a medial channel 28 and may contain a plurality of connections 26 where fittings 27 and apparatus and the like may be joined to the pipe 20, and also where the pipe 20 may connect to other sections of pipe 20 to extend the length thereof. When the invention is used in the drilling of a well to identify and measure components produced in a well drilling operation, the pipe 20 may communicate with a settling pond or similar collection body (not shown) which serves as the source of fluid 13. Further the pipe may communicate with other pipes (not shown) that carry drilling fluids and the like to and from the well bore, some of which may be under high pressure, such as downstream of a high pressure pump (not shown) and some of which maybe before or after the separation of particulated solids (not shown) from the fluid 14, such as by a vibrating screen (not shown) or a centrifuge (not shown).

As shown in FIG. 1, a temperature sensor 100 and a flow meter may be interconnected with the pipe 20 downstream of the source of fluid 13 and upstream of the grayloc support 80. The temperature sensor 100 and flow meter 90 are known apparatus and communicate with the medial channel 28 of the pipe 20 to monitor and sense the temperature of and movement of fluid 14 through the pipe 20. Information and data sensed by the temperature sensor 100 and the flow meter 90 are communicated to the computer 170.

In a first embodiment of the invention (FIG. 2), there are two spaced apart grayloc supports 80, 80A. Each grayloc support 80, 80A (FIGS. 3-5) is a fitting having a "cross" configuration defining an entry port 81, an exit port 82, a probe insertion port 83 and a blind port 84. Each of the ports 81, 82, 83, 84 communicate with a medial chamber 85 therebetween to allow fluid flow therethrough. An exterior circumference of each port 81, 82, 83, 84 defines a radially enlarged sealing flange 86 configured for engagement with a two part sealing clamp 87 to provide a fluid tight seal between the grayloc support 80 and the adjoining pipe 20, or an adjoining hub 89 to provide fluid containment.

Figure 2:
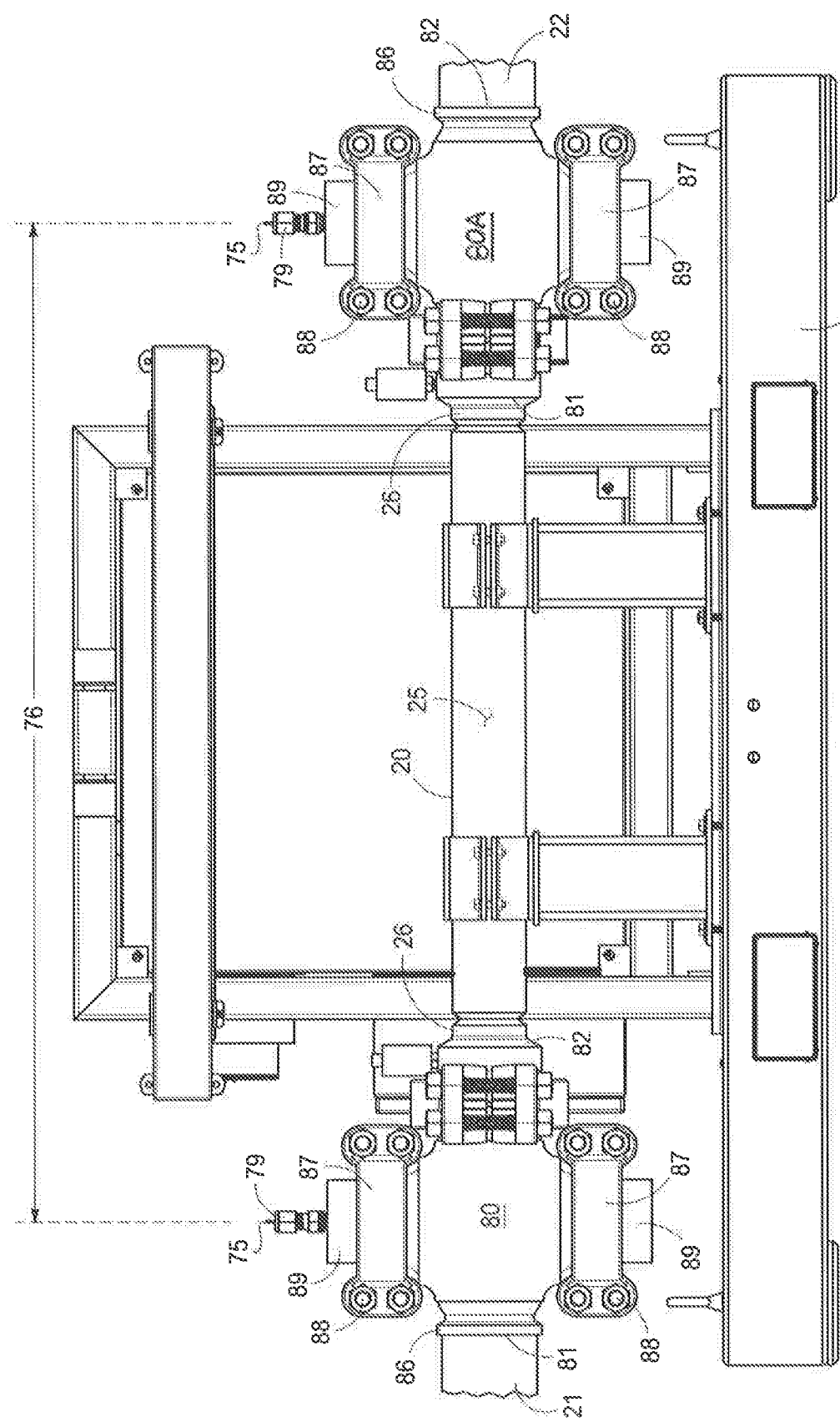
FIG. 2 is an orthographic front view of the two representative spaced apart grayloc supports and an electronics box mounted on a moveable support skid.

As shown in FIG. 2, the second grayloc support 80A communicates with the pipe 20 a known distance 76 downstream from the first grayloc support 80. The second grayloc support 80A has the same components and configuration as the first grayloc support 80 and therefore a detailed description of the second grayloc support 80A is omitted herein.

In configurations and embodiments where the apparatus is being used to identify and measure volume fraction constituents of a stationary fluid 14, such as a volume of fluid 14 contained within a storage tank (not shown), only one grayloc support 80 and probe 30 may be employed. If only a single grayloc support 80 is employed, it is necessary to have a flow meter 90 communicating with the pipe 20 if a velocity of the fluid 14 flowing through the pipe 20 is a required measurement.

In the first embodiment there are two spaced apart probes 30A, 30B, one probe 30 within each grayloc support 80, 80A. The first probe 30A and the second probe 30B are identical in configuration and function and therefore only the first probe 30A will be described in detail. These two spaced apart grayloc supports 80 allows velocity and volume to be calculated without use of a flow meter 90.

Figure 3:
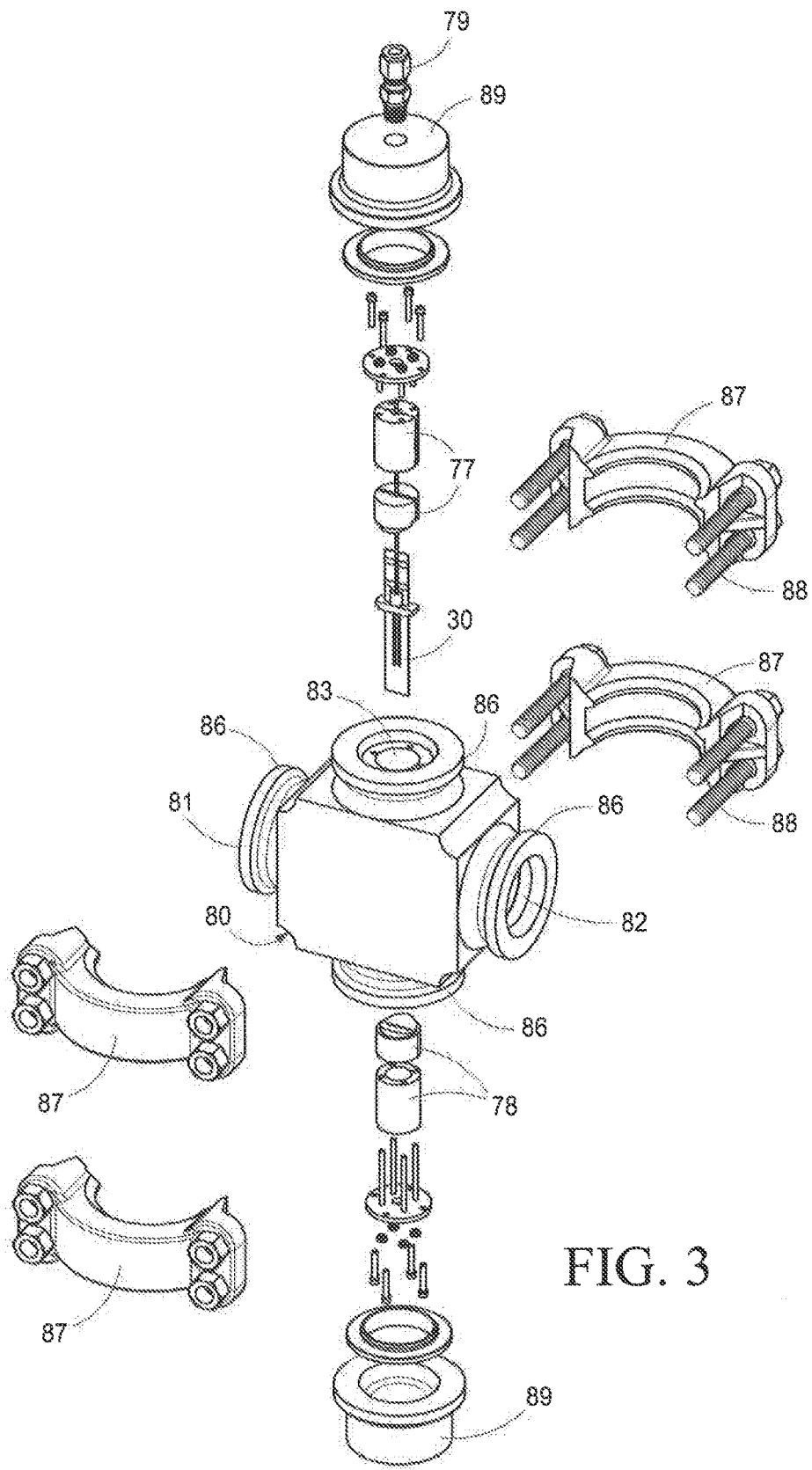
FIG. 3 is an exploded isometric front, side and top view of a grayloc support showing arrangement of the components and the probe.
Figure 4:
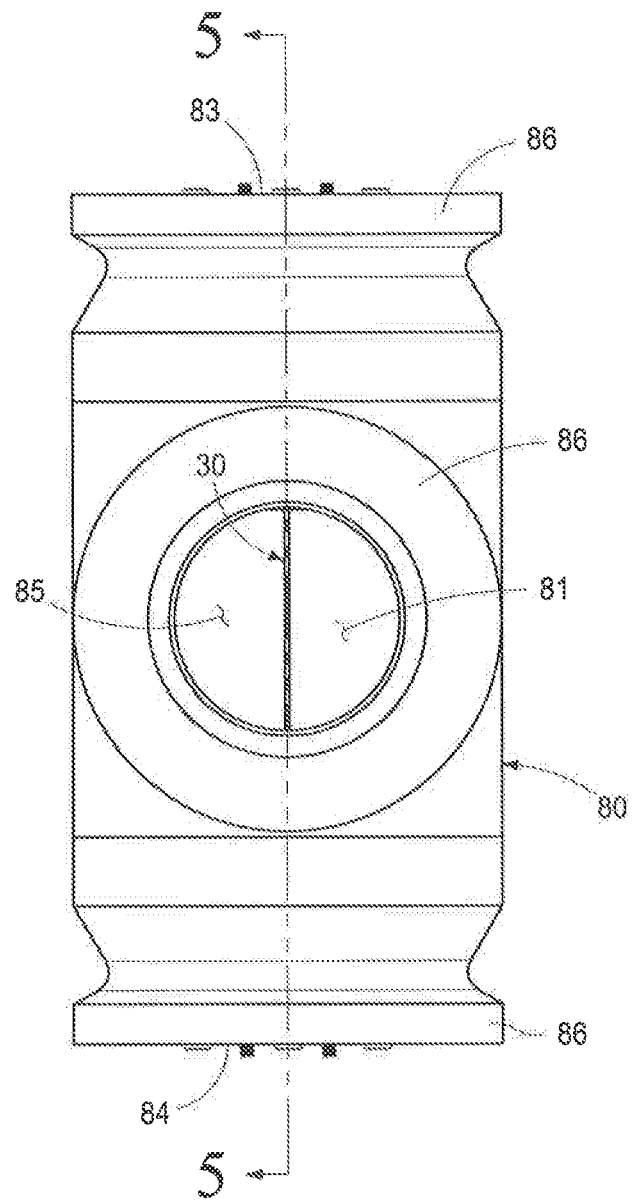
FIG. 4 is an orthographic side view of the assembled grayloc support of FIG. 3, less the sealed hubs.
Figure 5:
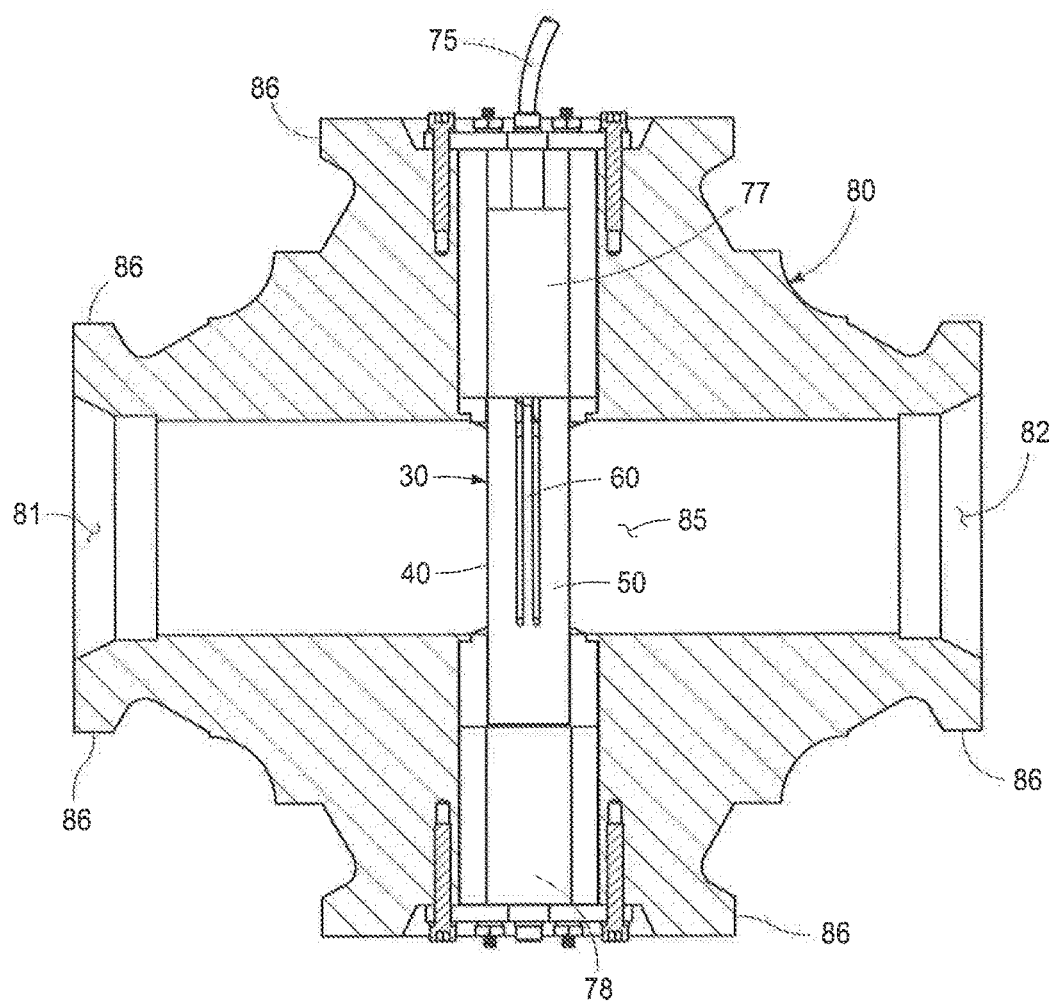
FIG. 5 is an orthographic cross section view of the assembled grayloc support of FIG. 4 taken on line 5-5 from FIG. 4.

As shown in FIGS. 3, 4 and 5, the probe 30 is positionally supported within the medial chamber 85 defined by the grayloc support 80 so that at least a portion of the probe 30 is exposed to the fluid 14 flowing through the grayloc support 80 medial chamber 85.

Figure 7:
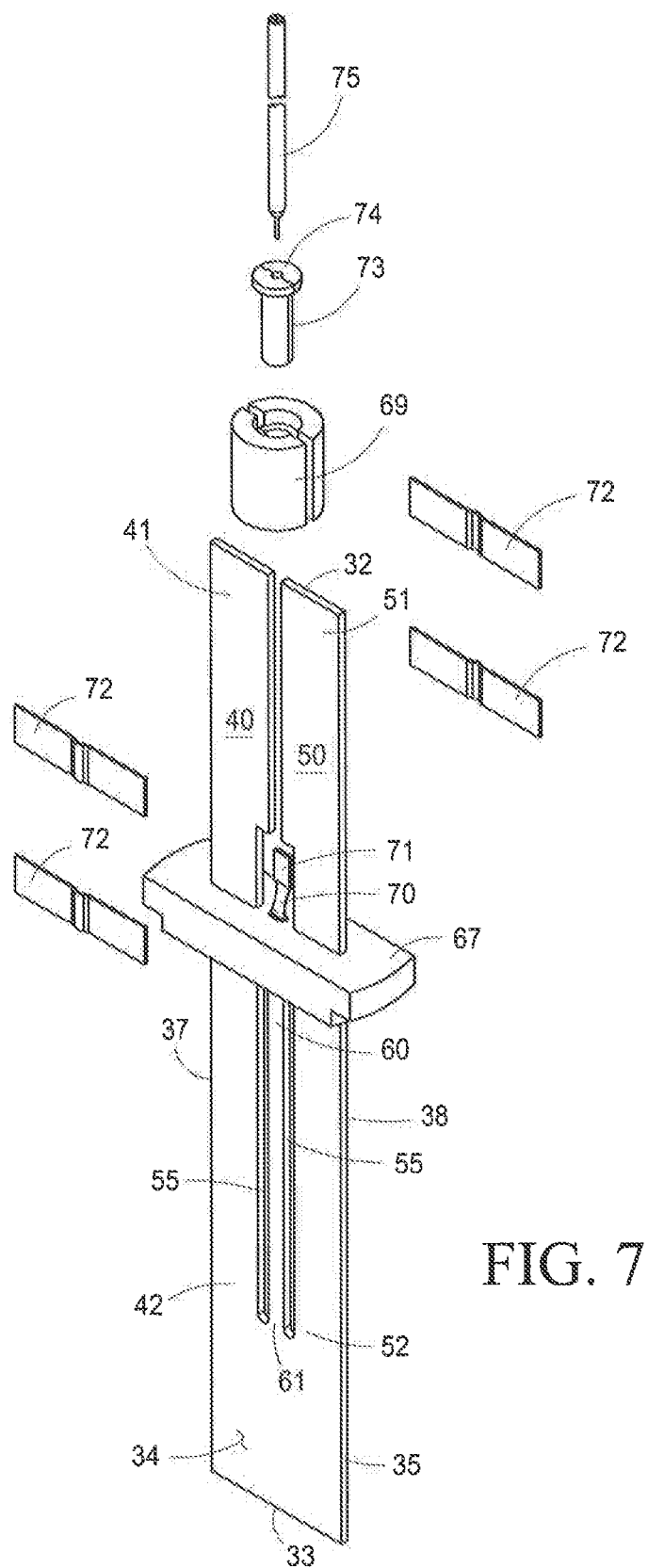
FIG. 7 is an exploded isometric front, side and top view of the probe of FIG. 6.
Figure 8:
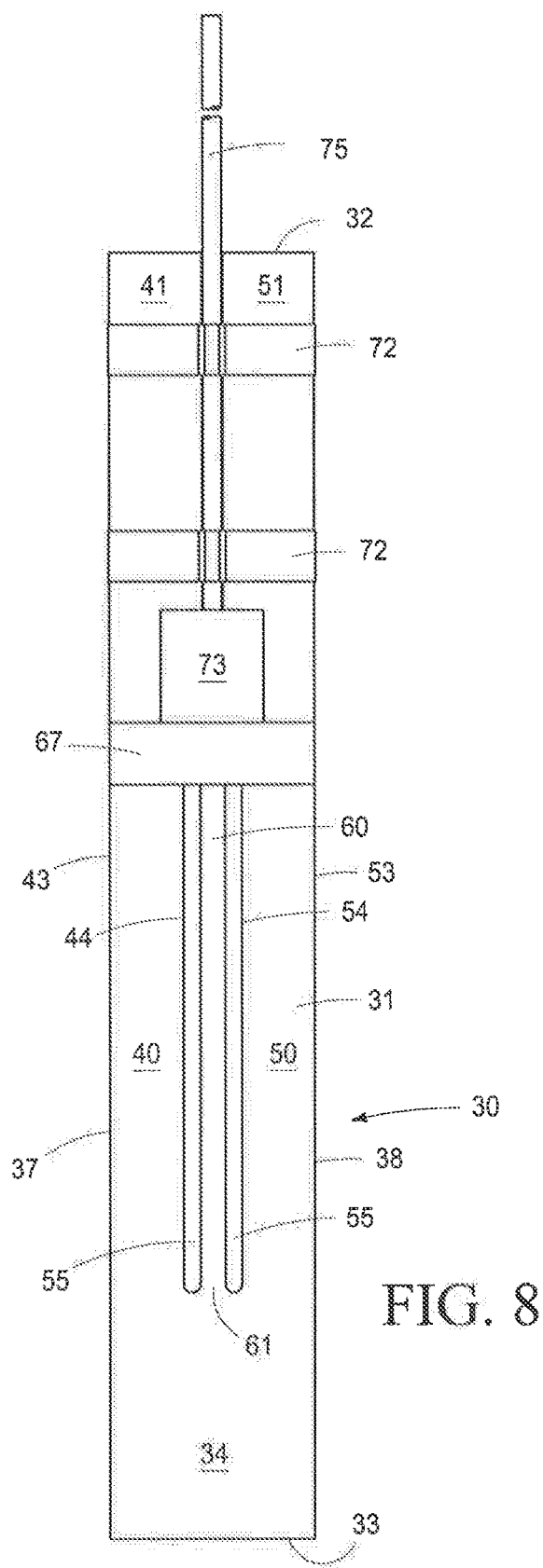

The probe 30 (FIGS. 6-8) has a body 31 that is generally planar and rectilinear. The body 31 has a first end 32 and an opposing second end 33, a first surface 34, and an opposing second surface 35 with a thickness 36 between the first surface 34 and the second surface 35. The body 31 further has a first edge 37, and an opposing second edge 38 and defines a dimensionally enlarged shoulder (not shown) in the first edge 37 and the second edge 38 spaced apart from the first end 32. The body 31 further defines an elongated medial slot 45 between a first ground plate 40 at the first edge 37 and a second ground plate 50 at the second edge 38. An elongated center conductor 60 is carried within the medial slot 45 and has a root end 61 that is structurally attached to the probe body 31 proximate the second end 33 between the first and second ground plates 40, 50 respectively, and the center conductor 60 has a free terminal end 62 within the medial slot 45 proximate to the body 31 first end 32. The free terminal end 62 of the center conductor 60 carries a conductor adaptor link 70 and a conductor weld pad 71 for electronic connection to a coaxial cable 75. The length of the center conductor 60 defines the active length of the probe 30. The first end 32 of the probe body 31 is known as the "active end" of the probe 30.

An elongated gap 66 is defined between each laterally outer edge of the center conductor 60 and a proximate edge of the first ground plate 40 and a proximate edge of the second ground plate 50. The gap 66 is engineered to provide optimum sensitivity to the detection of charges in volume flow constituents 15, 16, 17 by impedance measurements. The gap 66 is uniform along its length and is typically approximately 0.080 inches in width for oil 15, water 16 and natural gas mixtures. It is expressly contemplated however, other gap 66 widths may be used and/or engineered to match the impedances of other volume fraction constituents 15, 16, 17 to be identified and measured in the fluid 14.

A probe support block 67, which is generally rectilinear in configuration and formed of silicon carbide defines a generally medial slot (not shown) therein through which the probe body 31 first end 32 extends. The probe support block 67 frictionally engages with the dimensionally enlarged shoulders (not shown) defined in the probe body 31 so as to positionally maintain the probe 30 relative to the probe support block 67.

A coaxial cable 75 is electronically coupled with the conductor weld pad 71 so that signals may be transmitted to the probe 30 and received from the probe 30. Best shown in FIG. 7, the coaxial cable 75, and its attachment to the conductor weld pad 71, is positionally secured to the probe body 31 by an inner slip support 69, a pack 73 and a ring 74 so that the coaxial cable 75 is securely, and insulatively connected to the center conductor 60. In the current embodiment the pack 73 and ring 74 are formed of Teflon, but other materials such as PEEK may similarly be used and one contemplated. Plural support straps 72 (FIGS. 8, 9) spacedly arrayed on the probe body 31 further secure the coaxial cable 75 relative to the probe 30.

An active end support 77 (FIG. 3) frictionally engages the first end 32 of the probe 30 and extends over and about the coaxial cable 75 and an inner slip support 69. The active end support 77 aligns and positionally maintains the first end 32 of the probe body 31 within the medial chamber 85 of the grayloc support 80. (See FIG. 5). Similarly, a passive end support 78 frictionally engages with the second end 33 of the probe 30 and similarly aligns and positionally maintains the second end 33 of the probe 30 within the medial chamber 85 of the grayloc support 80. (FIG. 5).

As shown in FIG. 3, the assembled probe 30 and the active end support 77 are inserted into the grayloc support 80 probe insertion port 83 so that a medial portion of the probe 30 extends across the medial chamber 85 and is oriented so that the first surface 34 and second surface 35 are parallel to the flow of fluid 14 through the grayloc support 80 medial chamber 85. The probe 30 and end supports 77, 78 are secured within the grayloc support 80 medial chamber 85 by known means including, but not limited to, a spacer, a retainer plate and alignment pins. Such fastening means secure the first end 32 of the probe 30, and also secure the second end 33 of the probe 30 so that the probe 30 is supported from both the first end 32 and the second end 33 within the medial chamber 85. A fluid tight hub 89 is interconnected with the probe insertion port 83 sealing flange 86, and also with the blind port 84 sealing flange 86. Known, two part sealing clamps 87, and plural threaded fasteners 88 secure the hubs 89 to the sealing flanges 86 to provide a fluid tight seal therebetween. As can be seen in the drawings, the coaxial cable 75 extends through the hub 89 proximate to the first end 32 of the probe 30 by way of a CONAX pressure gland seal 79. The coaxial cable 75 electronically communicates with the probe 30 center conductor 60 and with the pulse emitter 120 and with the pulse sampler 150.

The grayloc entry port 81 communicates with the pipe 20 by means of a fluid tight connection 26 therebetween. Similarly, the exit port 82 communicates with a pipe 20 by means of a fluid tight connection 26 therebetween.

The second grayloc support 80A is also in fluid communication with the pipe 20 a known distance 76 downstream from the first grayloc support 80. The structure of the second grayloc support 80A, and the structure of the second probe 30B carried therein is the same as the aforementioned and described grayloc support 80 and first probe 30A.

The coaxial cables 75 that electronically communicate with each of the probes 30A, 30B are each electronically coupled with a pulse emitter 120 and also with pulse sampler 150. The pulse emitter 120 and the pulse sampler 150 may also be combined into a single apparatus commonly called a Time Domain Reflectometer (TDR), such as the EFP Signal Processor utilizing the CT100B software developed and manufactured by Mohr Test and Measurement of Richland, Wash., USA. Such TDR EFP Signal Processors are described in U.S. Pat. No. 4,786,857 issued Nov. 22, 1998, and U.S. Pat. No. 5,723,979 issued Mar. 3, 1998, and U.S. Pat. No. 6,144,211 issued Nov. 7, 2000, and U.S. Pat. No. 6,348,803 issued Feb. 19, 2002 and which were all invented by Charles L. Mohr (one of the joint inventors herein). The aforementioned issued US patents and the teachings therein are expressly incorporated herein by this reference.

Time domain reflectometry is known as an effective means for determining the level of a liquid, such as in a tank. Using time domain reflectometry, electrical pulses are conveyed along a transmission line to an electrically conductive probe 30. The electrical pulses are partially reflected when there is a change in the electrical impedance of the fluid 14 to which the probe 30 is exposed. The impedance change is associated with a difference in dielectric strength. "Electrical permittivity" is a technical term indicating the dielectric properties of the fluid 14. The electrical pulses produced by a time domain reflectometry system are affected by the dielectric constant of the surrounding fluid 14 in which the electrical pulse is traveling. The dielectric constant (permittivity) of the fluid 14 directly affects the propagation velocity of an electromagnetic wave as it travels along the probe 30. In time domain reflectometry systems, an electromagnetic pulse is propagated into and along the probe 30 which has a known length while measuring the time of arrival and the time of reflection from electrical discontinuities at two known, spaced apart, points. The first known point is where a coaxial cable 75 is attached to the probe 30. The second known spaced apart point, is a distal end of the probe 30. Since these locations are both known, one can calculate the propagation velocity of the electromagnetic wave and, as a result, calculate the apparent dielectric constant of the material undergoing tests and to which the probe 30 is exposed. Similarly, changes in the dielectric constant which relate to changes in the fluid 14 adjacent to and surrounding the probe 30 can also be determined. For example, the apparent dielectric constant provides a direct indication of the presence of identifiable types of fluids 14.

The pulse emitter 120 which may be incorporated into a TDR is an electronic apparatus that emits electronic pulses (not shown) which are conveyed to the probe 30 through the coaxial cable 75 at a preferred rate of approximately 500 to 800 samples per second depending upon the speed of computation and generating approximately 500 data points per sample. This means the electronic pulses are at increments of approximately 0.76 picoseconds. When the pulse emitter 120 emits a pulse (not shown) the pulse is conveyed along the coaxial cable 75 and to the probe 30 center conductor 60 through the conductor weld pad 71. The pulse travels along the center conductor 60 whereupon, depending upon the constituents 15, 16, 17 of the surrounding fluid 14 and the respective impedance (dielectric constants) of the constituents 15, 16, 17 to which the probe 30 is exposed, an electrical pulse reflection (not shown) is created when the pulse experiences a change in velocity due to a change in electrical impedance caused by a change in dielectric constant of the fluid 14 within the probe gaps 66 and surrounding the probe 30 active area. The pulse reflection is received from the probe 30 through the coaxial cable 75 and is communicated to the pulse sampler 150 where the reflection is sensed and recorded.

As the dielectric constant properties of the fluid 14 constituents 15, 16, 17 surrounding the probe 30 and within the probe gaps 66 change due to movement of the constituents 15, 16, 17 through the pipe 20, the velocity and distance traveled by the pulse in the increment of time between any two sequential pulses changes the apparent length of the probe 30. The pulse reflection, which indicates the end of the probe 30 or impedance change (the length of the probe in time), is conveyed along the coaxial cable 75 to the pulse sampler 150. Known computer logic within the computer 170 which is in electronic communication with the pulse emitter 120 and the pulse sampler 150 calculates the "length of the probe in time," Determination of the "length of the probe in time" is empirically representative of the dielectric constant of the fluid constituent 15, 16, 17.

The computer 170 has a database 172, which has stored therein, data and information on predetermined known dielectric constants of fluid constituents 15, 16, 17 and predetermined time delays generated by various dielectric constants. The database 172 also has stored therein predetermined known data and information of resonance points of various known volume fraction constituents 15, 16, 17 and the resonance points of various concentrations of the volume fraction constituents 15, 16, 17. The database 172 may also be a correlation or an algorithm wherein information may be correlated and/or compared.

The computer 170 determines the time difference between emission of the electrical pulse into the probe 30 by the pulse emitter 120, and receipt of the pulse reflection from the probe 30, by the pulse sampler 150. The determined time is then correlated by the computer 170, using the database 172 to known predetermined dielectric constants of known volume fraction constituents 15, 16, 17 which would similarly generate the determined time difference. The correlation of the determined time difference with information contained within the database 172 permits identification of the volume fraction constituent 15, 16, 17 fluid 14 by "matching" the determined time difference, with the predetermined known dielectric constant of various known constituents 15, 16, 17 of the fluid 14 which allows identification of the constituent 15, 16, 17.

The determined time difference between the electrical pulse emission from the pulse emitter 120 into the probe 30, and receipt of the electrical pulse reflection from the probe 30 by the pulse sampler 150 provides a "length of the probe" measurement which is shared with a detection algorithm within the computer 170 that compares the known "length of the probe" (which correlates to the impedance of the probe 30) to known dielectric constants, which may vary with salt content, and temperature as detected by the temperature sensor 100 in order to match the determined parameters with a known baseline to identify the volume fraction constituents 15, 16, 17 within the fluid 14. This first measure is time domain evaluation. It is the behavior of the electrical pulse within the probe 30, and the resulting length of the probe 30 which allows a first identification of the fluid constituents 15, 16, 17 passing through the grayloc support 80 medial chamber 85. As the fluid 14 passes around and about the probe 30 and through the gaps 66 between the center conductor 60 and proximate edges of the ground plates 40, 50, the pulse reflection, received by the pulse sampler 150 changes as the volume fraction constituents 14, 15, 16 of the fluid 14 change. The change is caused by the changing electrical impedance and changing dielectric constant of the fluid 14 that is in contact with the probe 30 and immediately surrounding the probe 30. However, it is known that the dielectric constants of such volume fraction constituents 15, 16, 17 are variable and dependent upon temperature and salt content and therefore using only one measure does not generate consistently reliably accurate results.

Figure 16:
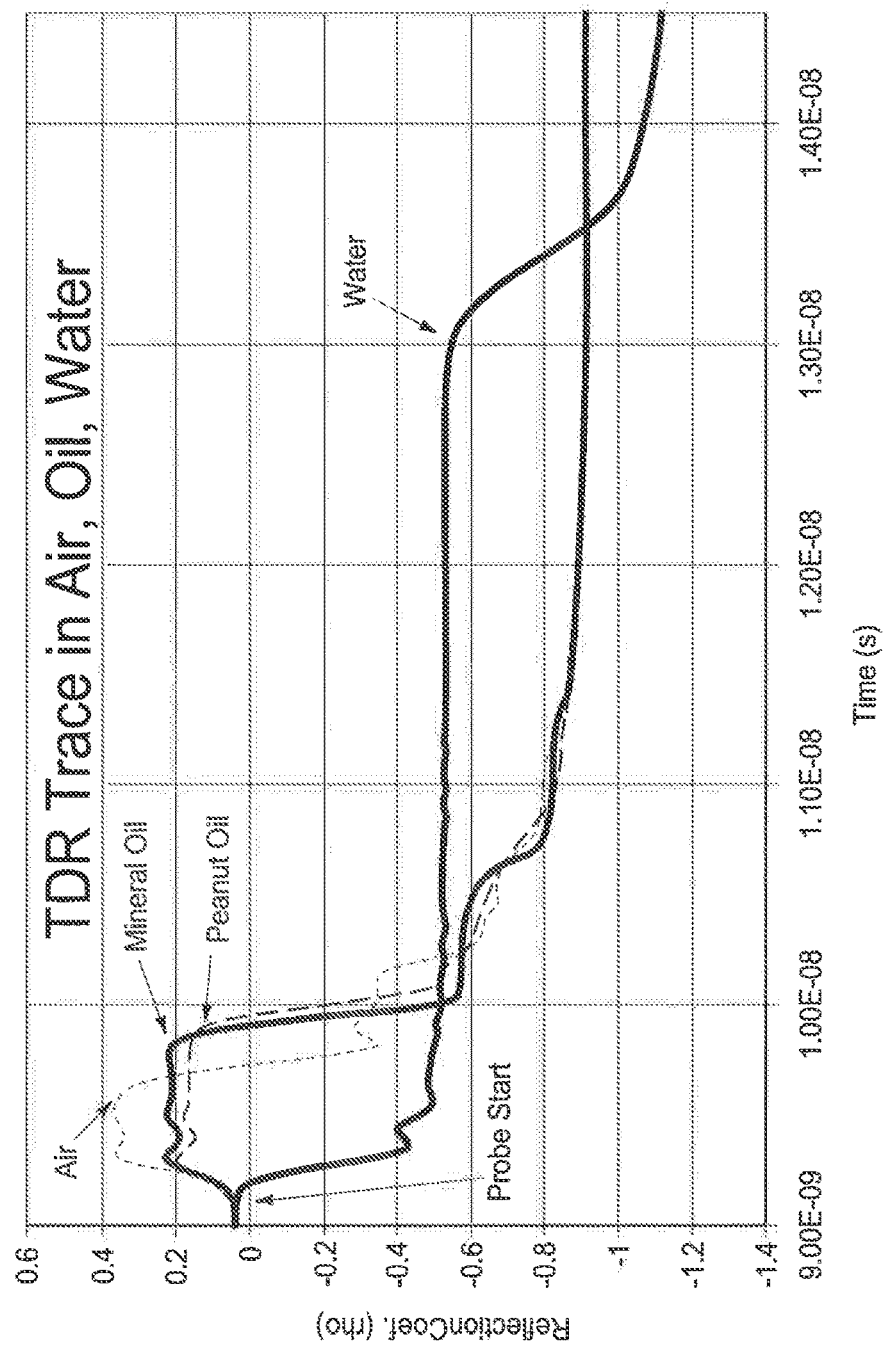
FIG. 16 is a time domain reflectance trace of an electrical pulse through the probe in a mixture of air, mineral oil, peanut oil and water showing the differences in the traces which allows identification of the components.
Figure 17:
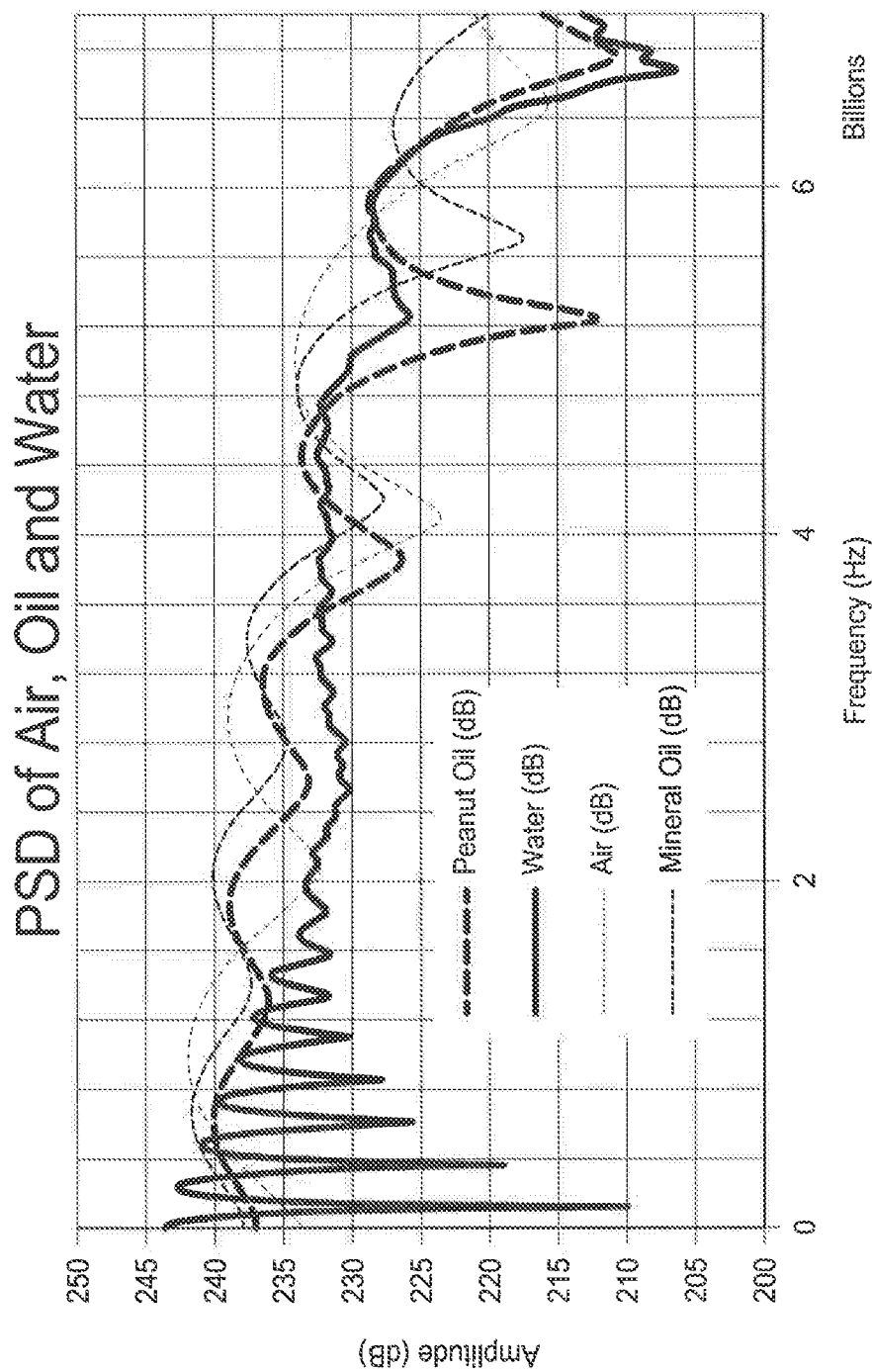
FIG. 17 is a power spectral domain (frequency domain evaluation) graph of the TDR traces of FIG. 16 after applying the FFT and PSD showing the resonance points of the components.
Figure 18:
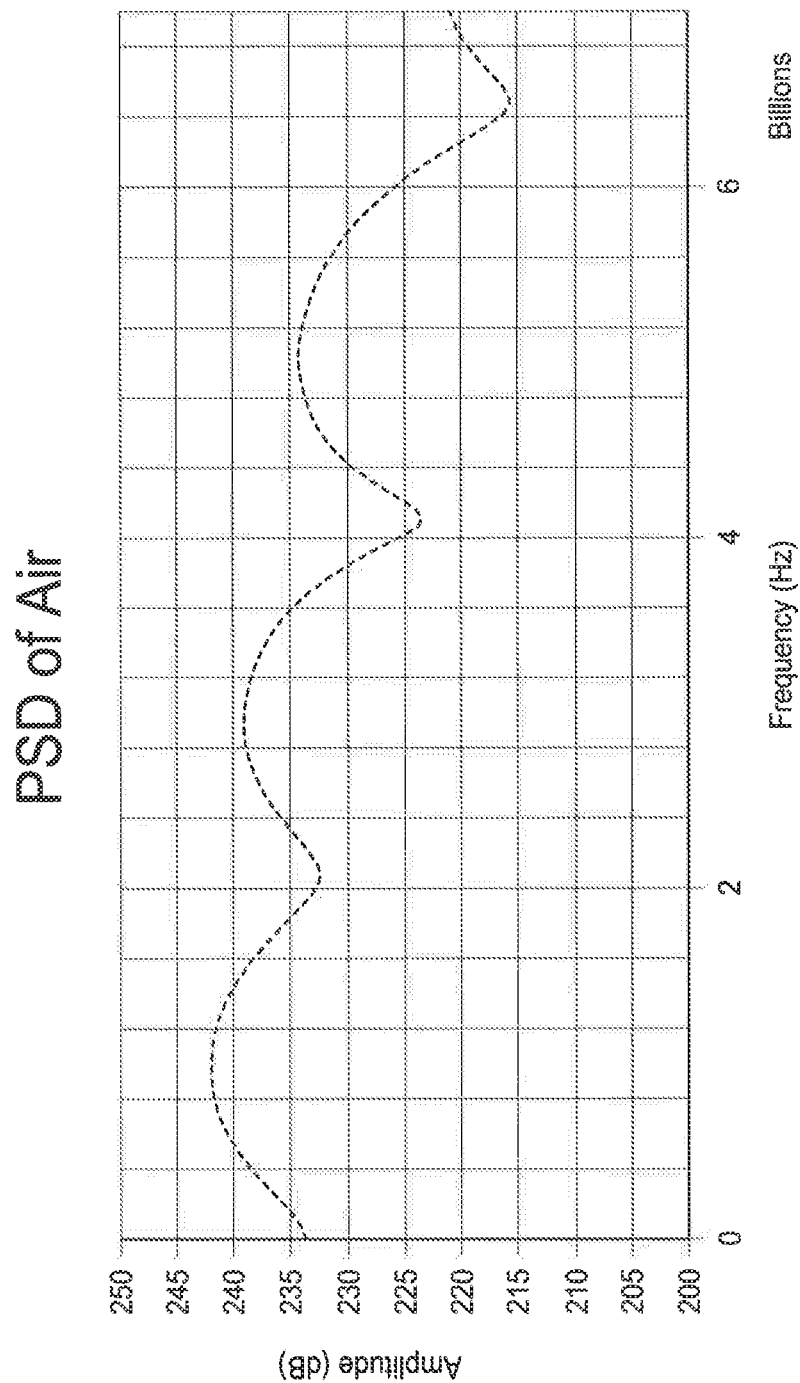
FIG. 18 is a power spectral domain (frequency domain evaluation) graph of the TDR trace of FIG. 11 showing the resonance points in air.
Figure 19:
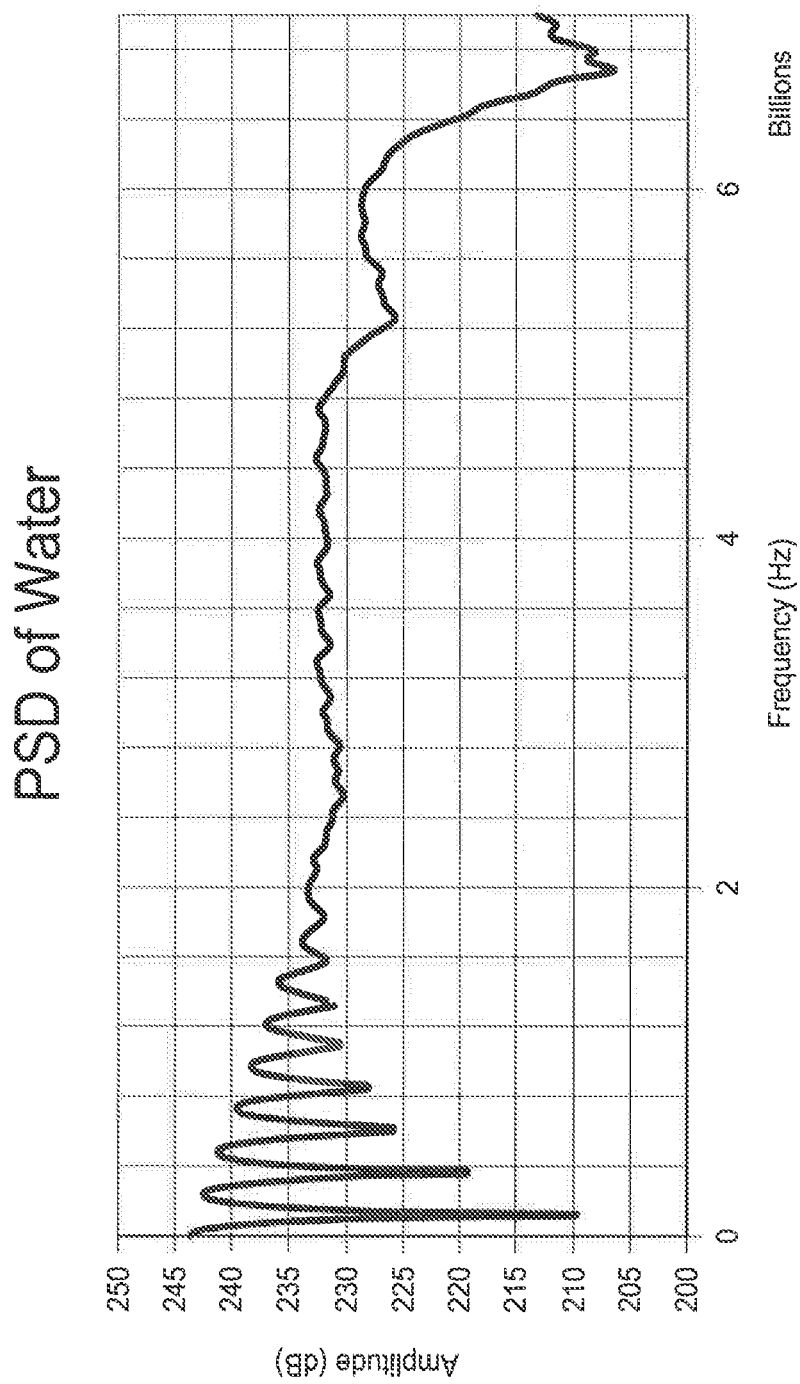
FIG. 19 is a power spectral domain (frequency domain evaluation) graph of the TDR trace of FIG. 12 showing the resonance points in water.
Figure 20:
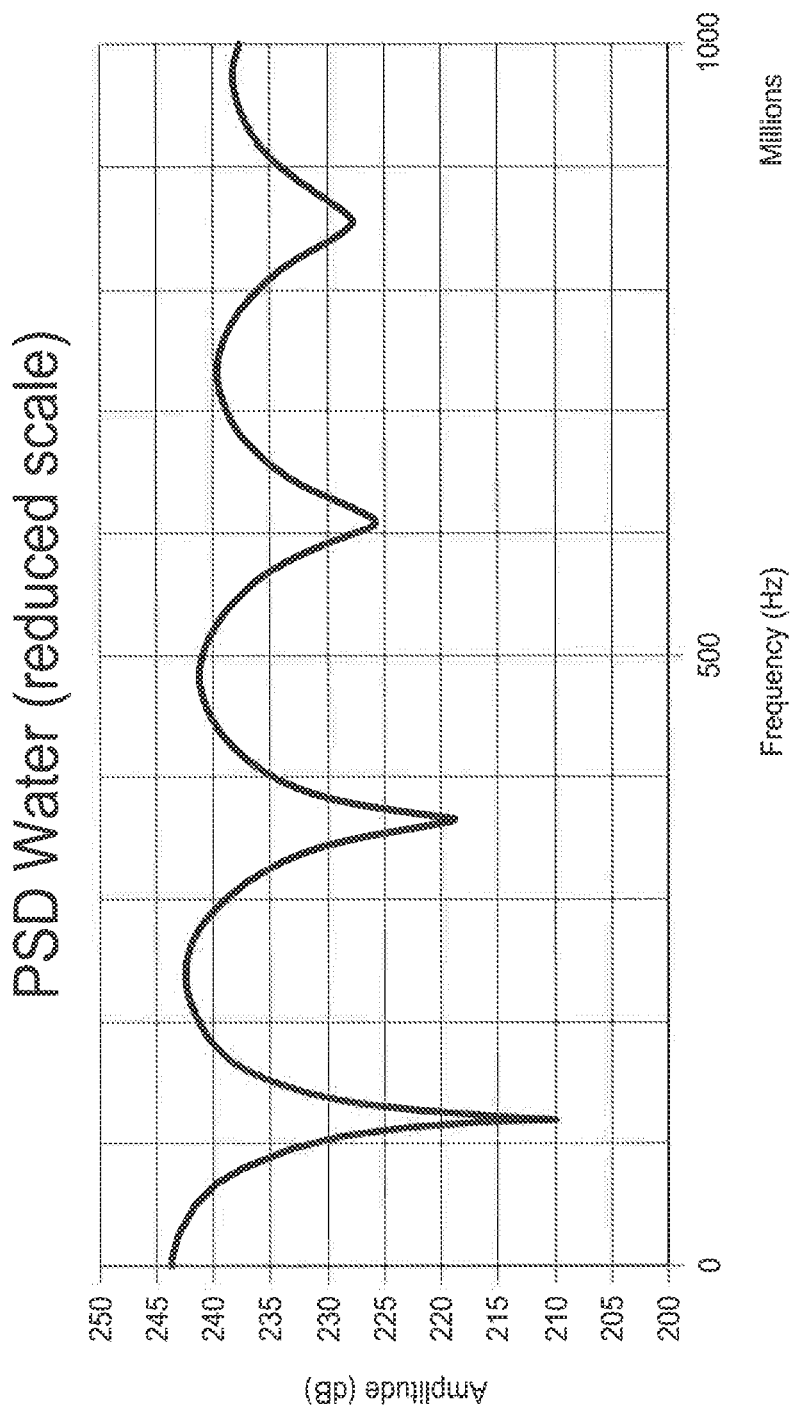
FIG. 20 is a reduced scale power spectral domain (frequency domain evaluation) of the probe in water, similar to that of FIG. 19 showing the resonance points.
Figure 21:
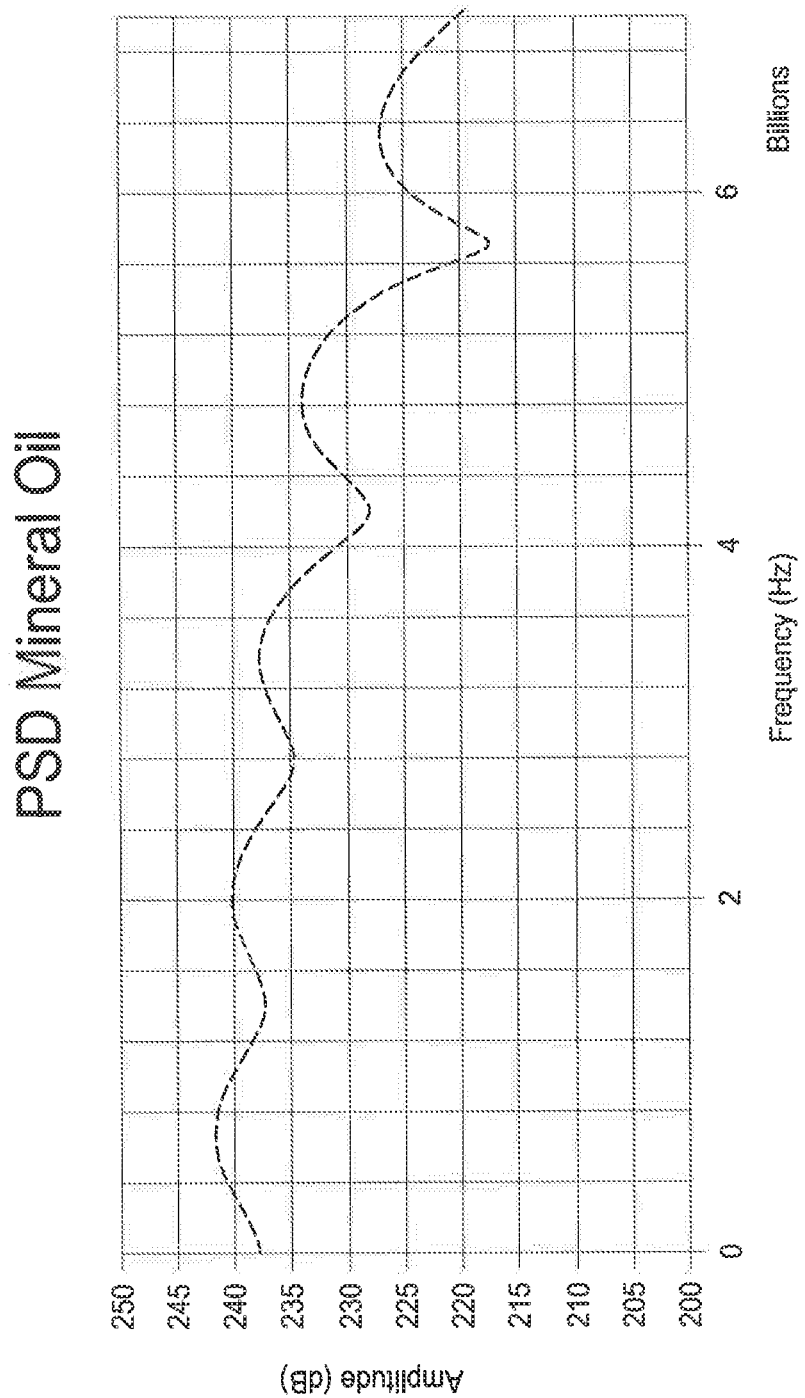
FIG. 21 is a power spectral domain (frequency domain evaluation) graph of the TDR trace of FIG. 13 showing the resonance points in mineral oil.

A second, frequency domain analysis takes advantage of the resonance of an electrical signal in the fluid 14 and allows measuring of a volume of the volume fraction constituent 15, 16, 17 within the fluid 14. By performing a Fast Fourier Transform (FFT) of the previously determined time delay of the pulse reflector, a sine wave frequency is determined. The frequency and amplitude of the sine wave signal (Power Spectral Density PSD) as a function of frequency allows different characteristic patterns of the constituents 15, 16, 17 to be identified. By examining the various resonance points as the frequency increases, the distance between the resonance points and the amplitude (strength) of the resonance points provide additional information as to various chemical compounds within the fluid 14 and allows identification and characterization of those various components, such as drilling fluids, drilling mud, oil 15, water 16, natural gas 17 and other components which may be newly appearing in the fluid 14 passing by the probes 30A, 30B. FIG. 16 shows the combined signals from a probe 30 in water 16, mineral oil, peanut oil and air. (Peanut oil and mineral oil were used in testing as representative oils to replicate petroleum). FIG. 17 shows the FFT transform of the same signals taken from the probe 30 in the different fluids 14 showing the Power Spectral Density (PSD) as a function of the frequency. As can be seen, the frequency/amplitude points of water 16, oil 15, air and peanut oil are distinctly different from one another, and changes in the relative fractions of the composition (concentrations) of the oil 15 causes a resulting shift in the resonance. The shift in resonance allows a measure of the fraction of each of the volume fraction constituents 15, 16, 17.

By performing the Fast Fourier Transform (FFT) of the reflected electrical pulse received by the pulse sampler 150, and by performing a Power Spectral Density (PSD) calculation, the frequency and amplitude of the resonance points can be identified.

The FFT takes a time-based plot (the determined time delay) and converts the time-based plot into a series of sine waves that duplicate the time history of the electric pulse as a series of frequency based sine waves with the maximums and minimums of the sine waves representing amplitude and resonance points of the volume fraction constituents 15, 16, 17 to which the probe 30 is exposed during the pulse and reflection thereof. The PSD calculation determines the average power, amplitude and frequency of the FFT transform. The first resonance point is identifiable because it has a wavelength that is equal to twice the active length of the probe 30. The relative permittivity of the fluid 14 is calculated by comparing the determined velocity in the fluid constituents 15, 16, 17 to the velocity of light in a vacuum using the following relationship between velocity and dielectric:

$$\frac{cf}{c} = \sqrt{1/ef} \; ;$$

where cf is the transmission speed of the pulse in the fluid 14, c is the speed of light in a vacuum, and ef is the relative permittivity or dielectric constant of the fluid 14. It is further noted that an inverse of the FFT allows recreation of the time history plot.

FIG. 16 shows combined time delay signals from a probe 30 exposed to water 16, oil 15 and air. The time delay shown in FIG. 16 is the transit time for the pulse to reach the end of the probe 30 and reflect therefrom. This time delay is proportional to the dielectric constant of the constituents 15, 16, 17 surrounding the probe 30. FIG. 17 shows a graphed Fast Fourier Transform and PSD of the signals shown in FIG. 16. FIG. 17 also shows the resonant peaks generated by the probe 30 in air, water 16 and oil 15.

As can be seen in FIG. 16, the dielectric constants are all different from one another, and changes in the relative volume fractions 15, 16, 17 causes a shift in the resonance peaks.

As shown in FIGS. 1 and 2, a second grayloc support 80A is interconnected with the pipe 20 a known distance 76 downstream from the first grayloc support 80. The second downstream grayloc support 80A carries a second probe 30B that is identical in configuration and function to the first probe 30A. The second probe 30B is similarly electronically coupled with a pulse emitter 120 and also with a pulse sampler 150, or a combined TDR, (Not shown). The pulse emitter 120 and pulse sampler 150 perform the same functions as the previously identified pulse emitter 120 and pulse sampler 150 to determine a time delay between the pulse emission into the probe 30B and receipt of a pulse reflection from the probe 30B by the pulse sampler 150. The determined time delay allows determination of the dielectric constants of the constituents 15, 16, 17 of the fluid 14 by comparison to the known, pre-determined time delay information stored in the database 172 information that is assessable by the computer 170. Each probe 30A, 30B may be, coupled with, a separate pulse emitter 120 and a separate pulse sampler 150 which as noted previously may be combined within a single TDR. (Not shown). The computer 170, and the database 172 accessible thereby, is electronically coupled with both pulse emitters 120 and both pulse samplers 150 (both TDR's) so as to correlate the determined time delays from each probe 30A, 30B with the information within the database 172.

The known distance 76 between the first probe 30A and the second probe 30B allows the instant invention to continuously, and in real time, determine the volume of each volume fraction constituent 15, 16, 17 moving through the pipe 20. Because the computer 170 is electronically coupled with the first probe 30A and with the first pulse emitter 120, and the first pulse sampler 150, and also with the second probe 30B and the second pulse emitter 120, and the second pulse sampler 150, the computer 170 is able to determine a time delay between the first probe's 30A identification of a specific volume constituent 15, 16, 17 and the second probe's 30B identification of the same volume constituent 15, 16, 17 subsequent to the first probe 30A identification. Because the interior diameter 23 of the medial channel 28 is known, the total volume of the fluid 14 moving through the pipe 20 by unit of time may be calculated once the velocity of the fluid 14 in the pipe 20 is determined. The time delay between the first probe 30A identifying a specific volume constituent 15, 16, 17 and the second probe 30B subsequently identifying the same volume constituent 15, 16, 17 is used in conjunction with the known distance 76 and known volumetric formulas to determine the volume of identified volume fraction constituents 15, 16, 17 moving through the pipe 20. The probe's 30A, 30B detection of a change in probe length, as described earlier, is indicative of a different volume fraction constituent 15, 16, 17 being identified by the probe 30A, 30B and that information, which is communicated to the computer 170 allows identification of the volume constituent 15, 16, 17, and the volume of the volume of that constituent 15, 16, 17 to be determined.

The time domain evaluation, and the frequency domain evaluation, provide two separate methods to identify volume fraction constituents 15, 16, 17 in the fluid 14 and further allows a determination of a volume of each volume fraction constituent 15, 16, 17 to be determined as the fluid 14 moves through the pipe 20, on a continuous basis. The frequency domain evaluation further allows the concentration of the various volume fraction constituents 15, 16, 17 in the fluid 14 to be determined by correlating the resonance points of the fluid constituents with known resonance points of known constituent concentration within the database 172.

Each probe 30A, 30B has a probe body 31 (FIGS. 6-10) that is generally rectangular in shape and formed of a metallic alloy and is preferably approximately 0.050 inches thick from the first surface 34 to the second surface 35 and approximately 1.00 inches in width from the first edge 37 to the second edge 38. The probe body 31 is preferably formed entirely of Inconel® alloy 725 which is highly resistant to the corrosive environment to which the probe body 31 may be exposed during operation. Further, a desirable and durable dielectric oxide coating (not shown) is formed on the probe of body 31 extending entirely thereabout. Inconel® alloy 718 may also be used, but Inconel® alloy 725 is preferred. Inconel® alloy 725 and Inconel® alloy 718 are available from Megamex Specialty Metals of Humble, Tex.

The method of forming the probe 30, which carries the durable dielectric oxide coating on its outer surfaces 34, 35, includes the steps of cutting the desired probe 30 shape from the desired metallic alloy and then oxidizing cleaning the probe body 31 at approximately 1,750° to 2,000° Fahrenheit in air for one to three hours in order to form the highly electrically resistive oxide surface covering the entire body 31 of the probe 30. The temperatures used in formation of the oxide coating reduce cracking of the oxide coating and prevents embrittlement caused by grain growth. Following the one to three hour heat treatment, the probe body 31 is cooled to less than 1,000° Fahrenheit. Subsequently, the probe body 31 is heated in air to 1,325° Fahrenheit for a period of 8 hours. Thereafter, the probe body 31 is air cooled in an oven to ambient temperature. The heat treatment process forms a chrome alumina oxide coating covering the entire probe body 31 to insulate the probe body 31 in the fluid 14. The oxide coating is preferably approximately 0.5 mm to approximately 3 mm thick and is believed to have a chemical composition of approximately CrMoNbTiAl.

It is desirable that the probe body 31, carrying the chrome alumina oxide coating has an impedance of approximately 90 ohms in air, which allows use of a 90 ohm coaxial cable 75 for interconnection with the pulse emitter 120 and the pulse sampler 150. The use of a 90 ohm coaxial cable 75 allows the probe 30 to measure 100% water 16; water 16 containing very little oil 15; 100% oil 15; and oil 15 containing very little water 16. Providing for such a wide range of measurements of water/oil mixtures allows the probe 30 to measure a full range of "water cuts". Further, the ability to operate at 90 ohms allows the probe 30 to identify drilling fluids (not shown) and components thereof and also identify and measure effective water 16 content within drilling fluids. The probe's 30 the ability to measure water content allows the probe 30 to be used in stationary operations, such as to measure the water 16 content of a standing pool of fluid 14, such as fuel in a fuel tank (not shown) that may be contaminated with an unknown amount of water 16. The probe's 30 ability to detect and measure drilling fluids/drilling muds (not shown) allows the instant invention and probes 30 to be used in the drilling of hydrocarbon producing wells, as well as the use in hydrocarbon producing wells that are in production.

Figure 6A:
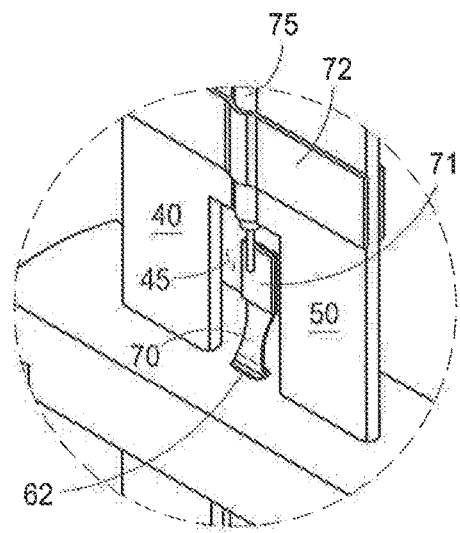
FIG. 6A is an enlarged isometric view of the probe and support block showing details of the coaxial cable connection.
Figure 6:
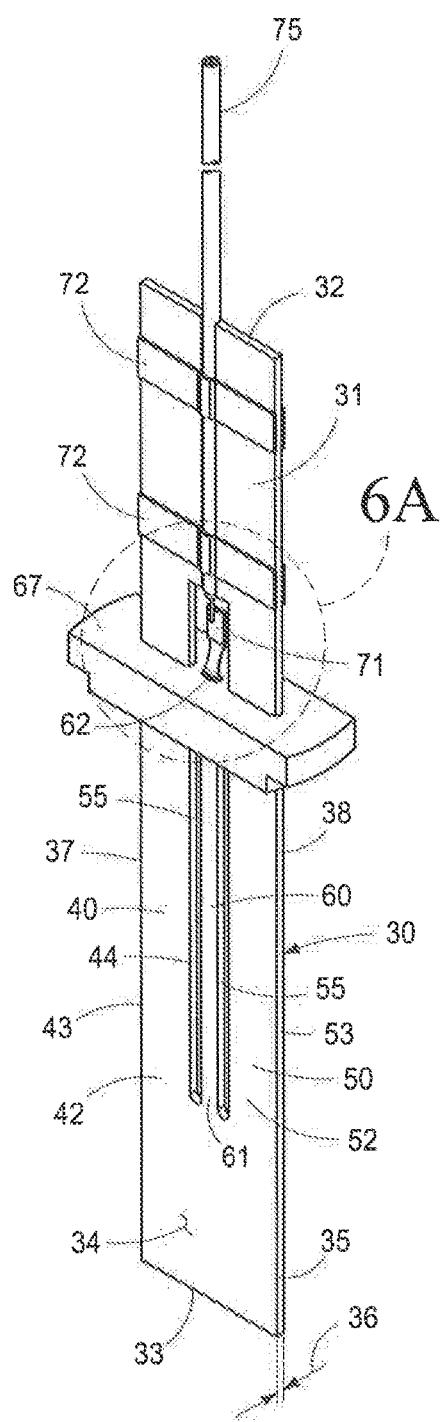
FIG. 6 is an isometric front, side and top view of a first configuration of a probe and support block.
Figure 9:
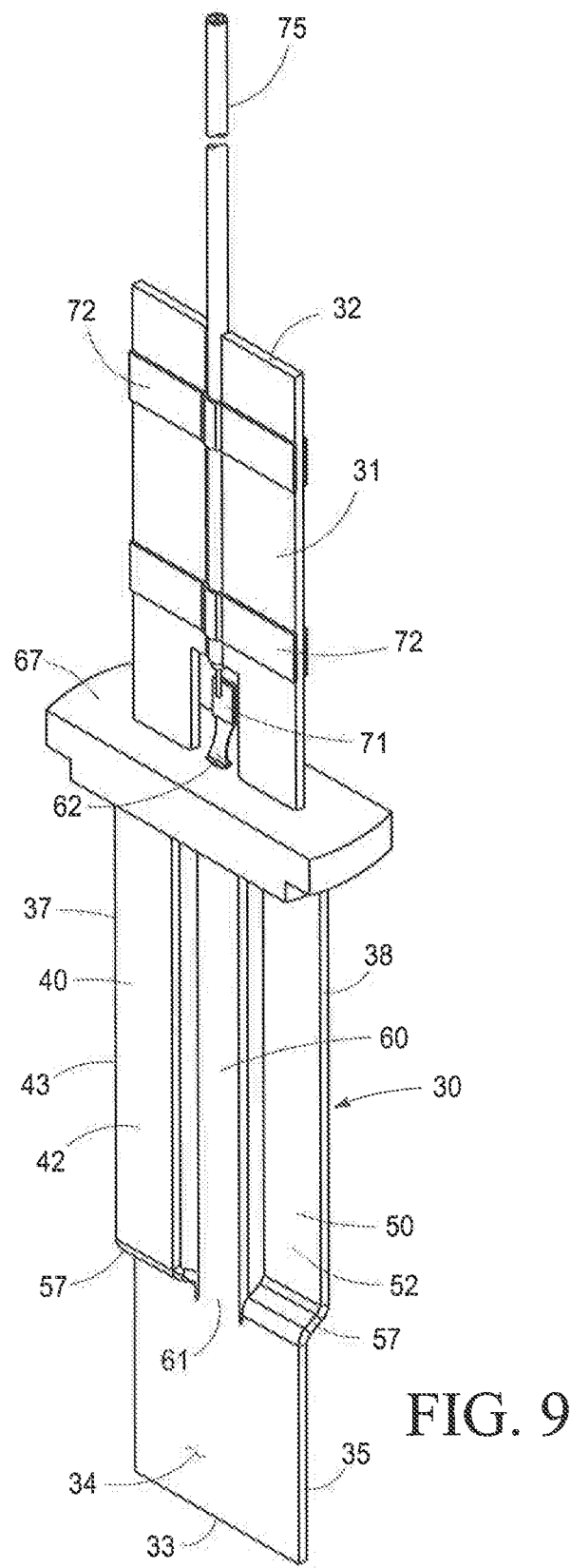
FIG. 9 is an isometric front, side and top view of a second configuration of probe having offset ground plates.
Figure 10:
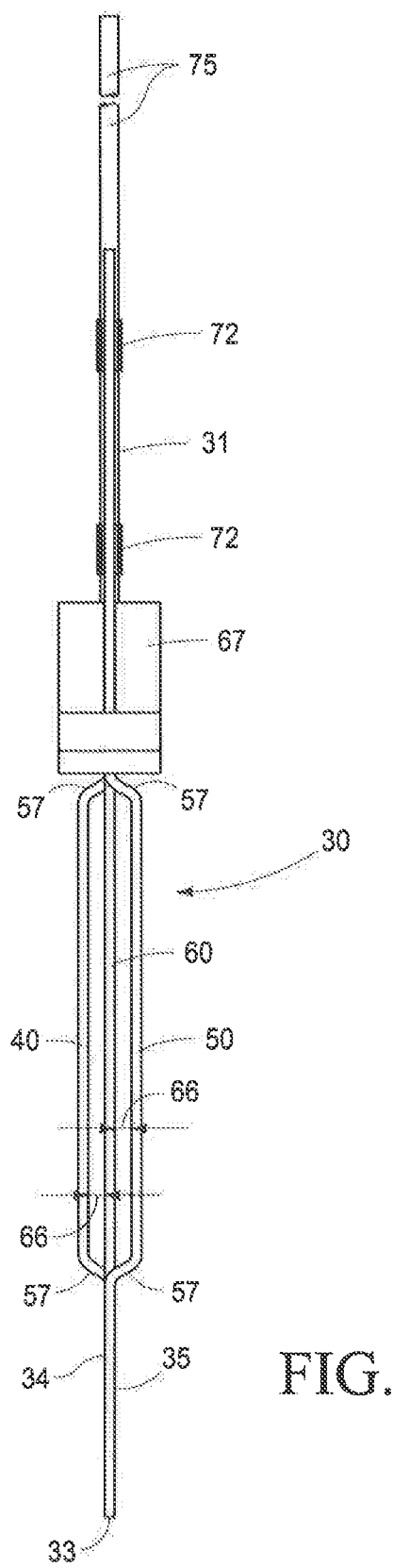
FIG. 10 is an orthographic side view of the second configuration of blade probe of FIG. 9, showing the open structure formed by offsets of the ground plates relative to the center conductor.
Figure 11:
FIG. 11 is a time domain reflectance trace of an electrical pulse through the probe in air showing the start point and the end point.
Figure 12:
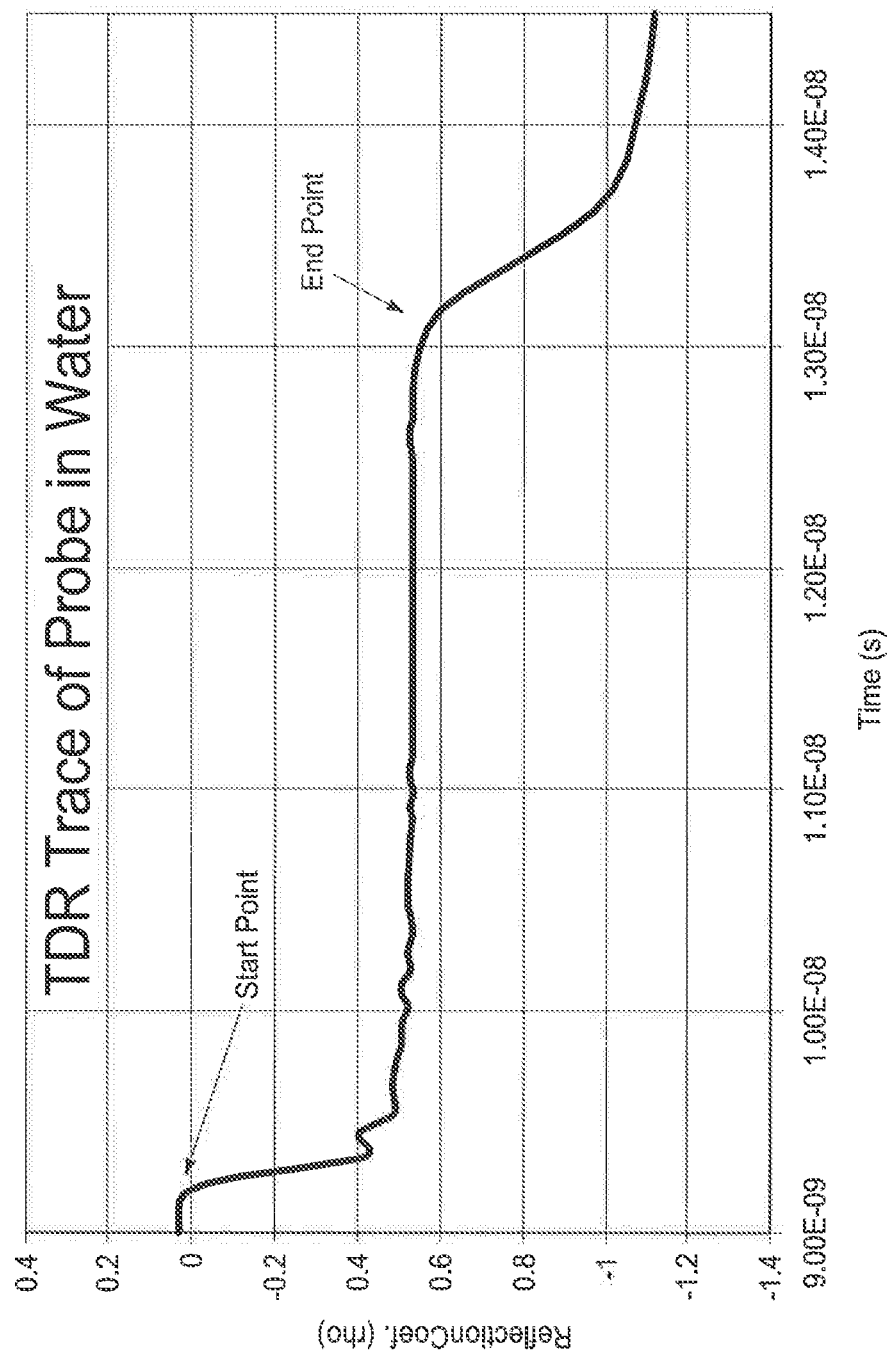
FIG. 12 is a time domain reflectance trace of an electrical pulse through the probe in water showing of the start point and the end point.
Figure 13:
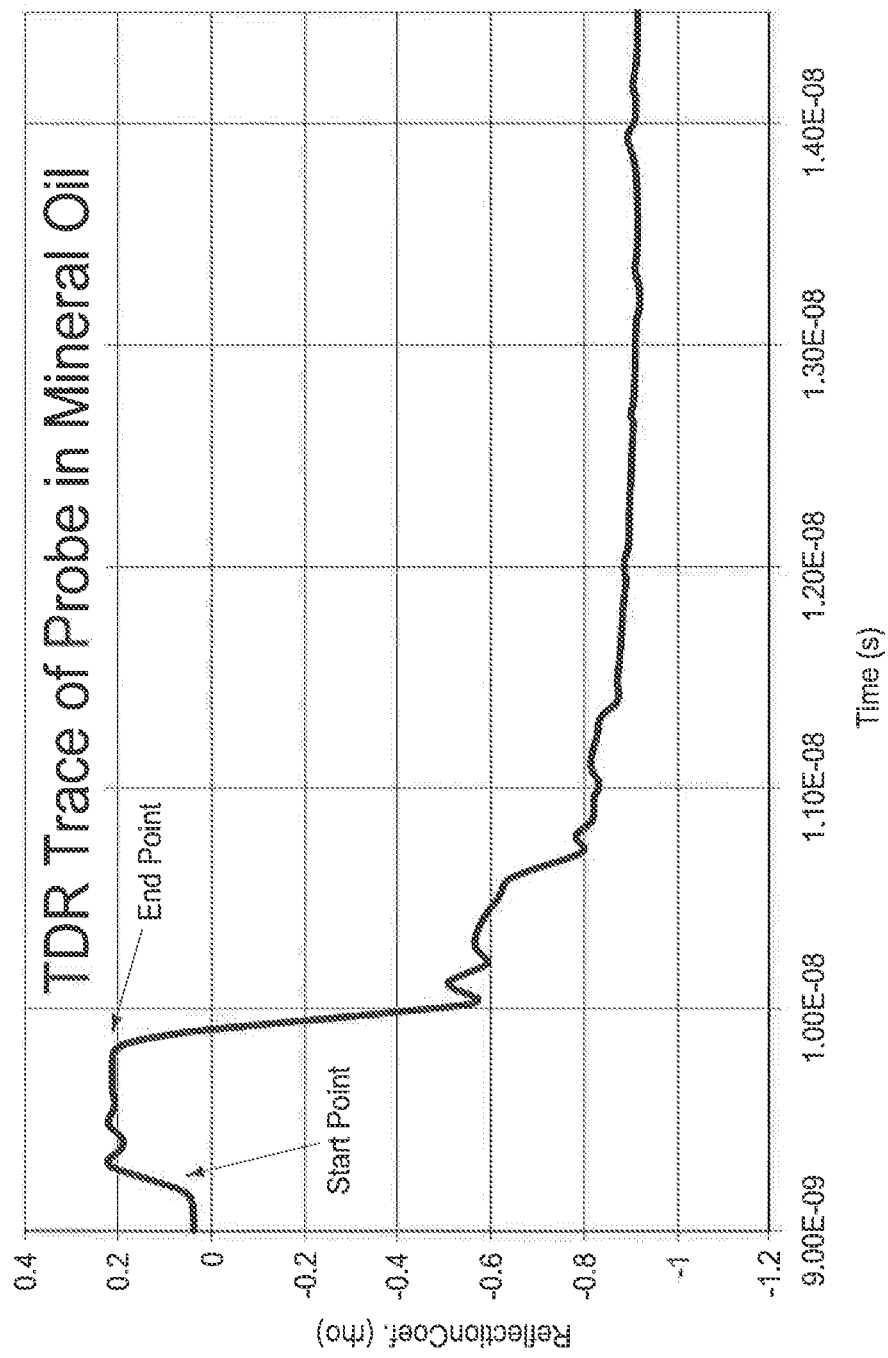
FIG. 13 is a time domain reflectance trace of an electrical pulse through the probe in mineral oil showing the start point and the end point.
Figure 14:
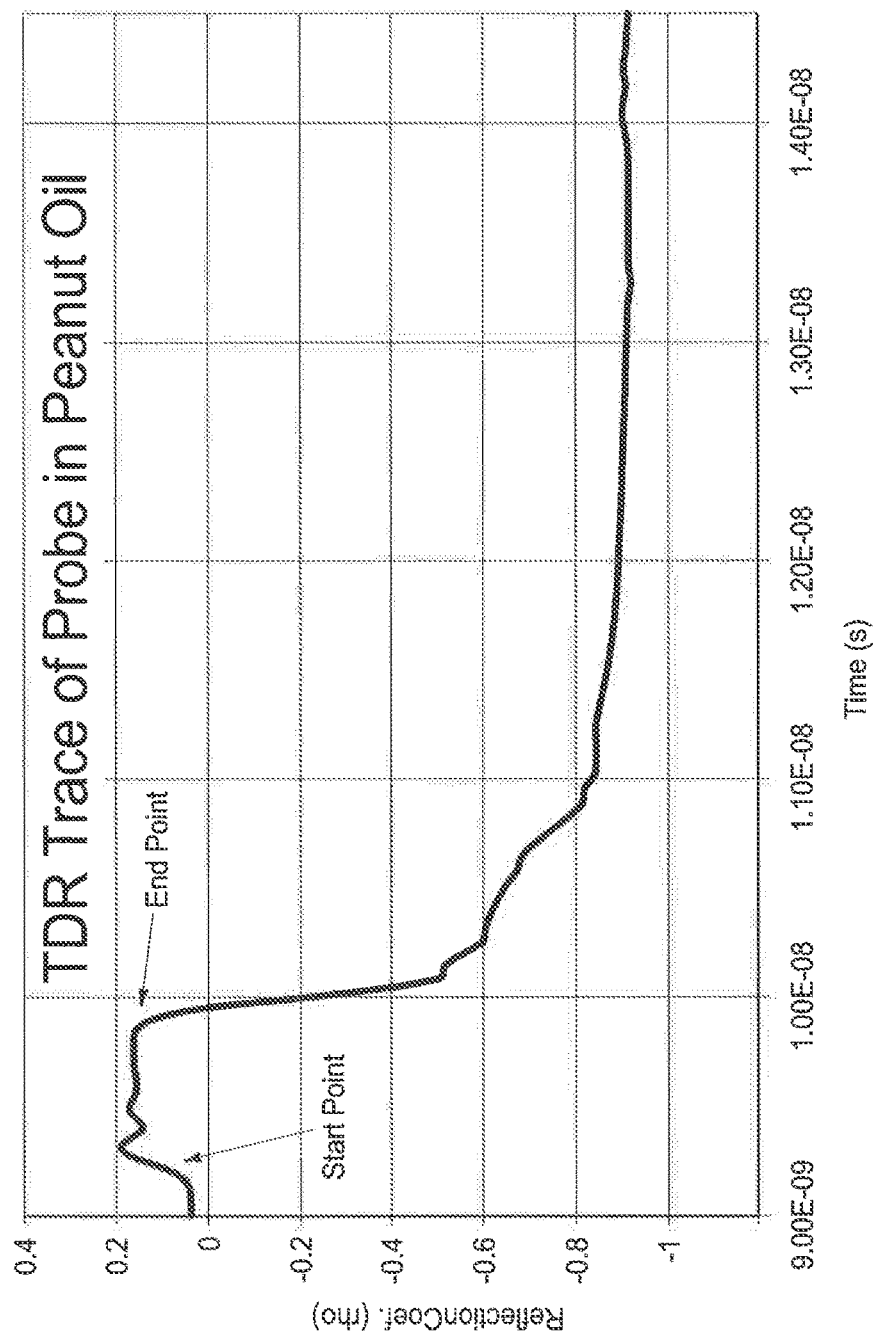
FIG. 14 is a time domain reflectance trace of an electrical pulse through the probe in peanut oil showing the start point and the end point.
Figure 15:
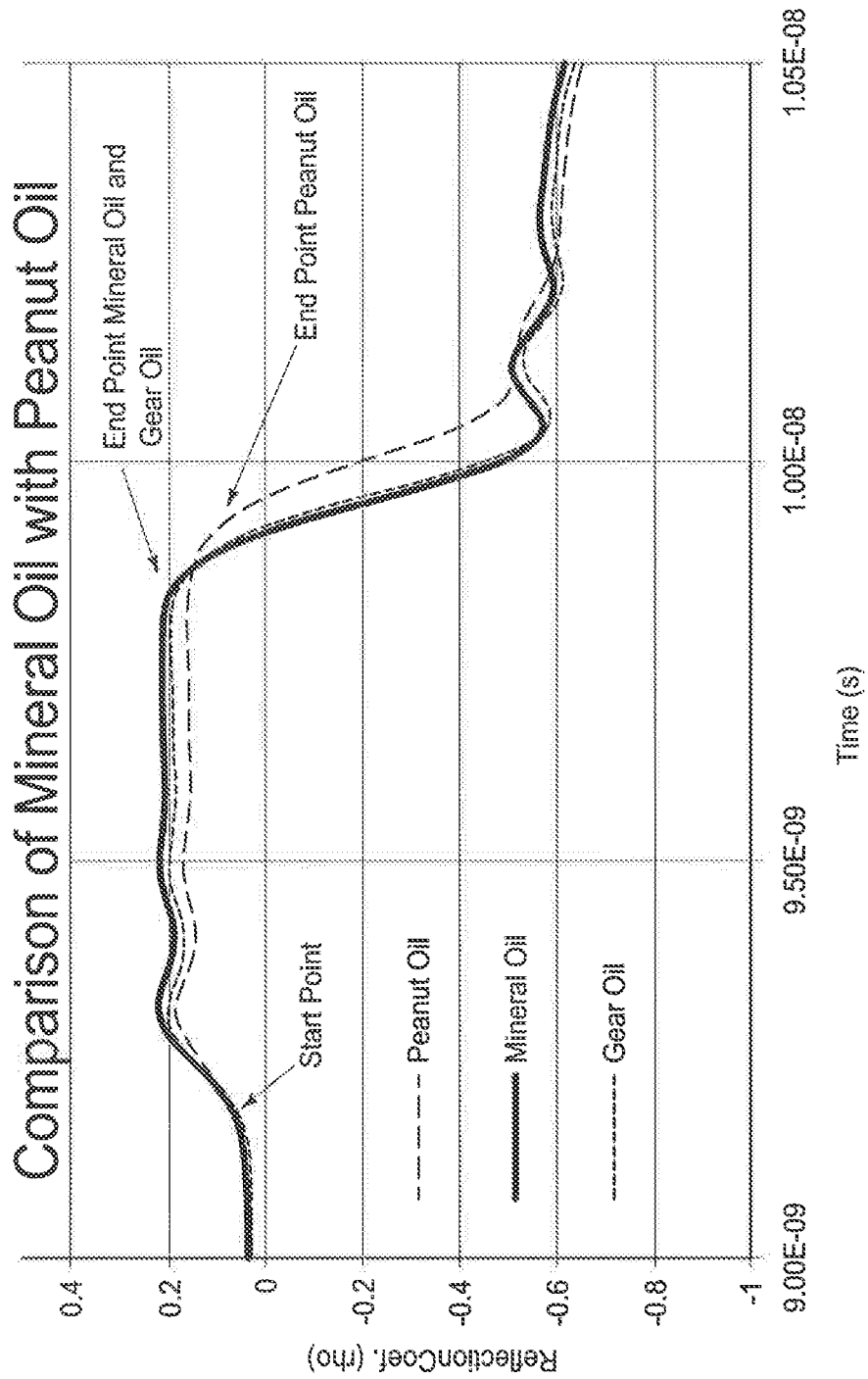
FIG. 15 is a comparison time domain reflectance trace of an electrical pulse through the probe in peanut oil, mineral oil and gear oil showing the start point and the endpoint and showing the similarity in the traces amongst the different types of oils.

As shown in FIGS. 9 and 10, a second design of probe 30 is also contemplated herein. This second probe 30 design is intended to reduce potential (clogging) due to particulates and solids within the fluid 14 moving through the medial channel 28 of the pipe 20 and the grayloc supports 80 and is particularly useful for use in drilling operations when drilling mud is a component of the fluid 14. In the second design (FIGS. 9, 10) the first ground plate 40 is offset toward the first surface 34 relative to the center conductor 60 defining a gap 66 of approximately 0.080 inches between a proximate edge of the first ground plate 40 and the center conductor 60. Similarly, the second ground plate 50 is offset toward the second surface 35 by a distance of approximately 0.080 inches to define a gap 66 between the proximate edge of the second ground plate 50 and the center conductor 60. The offsetting of the first ground plate 40 and the second ground plate 50 relative to the center conductor 60 is facilitated by bends 57 at a bottom portion of the offset portion, and at an upper portion of the offset portion so that only the active portion of the probe body 31 is laterally offset to allow fluid 14 to flow through the gap 66. (FIG. 10). In other aspects, the second probe design (FIG. 10) is the same as that of the first probe design (FIG. 6).

OPERATION

Having described the structure of an apparatus for identifying and measuring a volume fraction constituent of a fluid, its operation may be understood.

A source of fluid 13 is provided and is interconnected with a pipe 20 defining the medial channel 28 to provide fluid 14 moving therethrough, the fluid 14 having a volume fraction constituent 15, 16, 17 that is desired to be identified and measured, and wherein the volume fraction constituent 15, 16, 17 has previously calculated and known dielectric constant, and a previously calculated and known resonance points, and wherein information about the previously calculated and known dielectric constant and previously calculated and known resonance points of the volume fraction constituent 15, 16, 17 is stored in, and is accessible from a database 172.

A first probe 30A is exposed at least in part to the fluid 14 moving through the pipe 20, the first probe 30A having a known active length, and the first probe 30A is positionally maintained within a medial chamber 85 defined by a grayloc support 80 communicating with the medial channel 28 of the pipe 20, so that the fluid 14 flows therethrough and thereabout and therepast the first probe 30A.

A second probe 30B is also exposed at least in part to the fluid 14 moving through the pipe 20, a known distance 76 downstream of the first probe 30A, the second probe 30B having an known active length, and the second probe 30B is positionally maintained within a medial chamber 85 defined by a second grayloc support 80A that also communicates with the medial channel 28 of the pipe 20, a known distance 76 downstream of the first grayloc support 80 so that the fluid 14 flows therethrough, and thereabout and therepast the second probe 30B.

A back pressure regulator 110 communicating with the medial channel 28 of the pipe 20 maintains fluid pressure about the probes 30A, 30B at a pressure at least equal to the pressure of the source of the fluid 13 to prevent boiling of the fluid 14 within the pipe 20 to prevent formation of steam within the pipe 20, because steam has a dielectric constant that is similar to the dielectric constant of natural gas 17 which would make it difficult to distinguish between a volume of natural gas 17 and a volume of steam.

The first electrical pulse emitter 120 electronically generates an electrical pulse which is conveyed to the first probe 30A through the coaxial cable 75. The electrical pulse then generates an electrical pulse reflection upon interacting with a changed electrical impedance (which is indicated as an end of the first probe 30A) and which is caused by a change in sensed dielectric constant of the volume fraction constituent 15, 16, 17 to which the first probe 30A is exposed. The first electrical pulse sampler 150 receives and senses of the electrical pulse reflection.

Similarly, the second electrical pulse emitter 120 electronically generates an electrical pulse which is conveyed to the second probe 30B through the coaxial cable 75. The electrical pulse similarly generates an electrical pulse reflection upon interacting with the changed electrical impedance (which is indicated as an end of the second probe 30B) and which is caused by a change in sensed dielectric constant of the volume fraction constituent 15, 16, 17 to which the second probe 30B is exposed. The second electrical pulse sampler 150 receives and senses of the electrical pulse reflection.

The computer 170 is electronically coupled with the first probe 30A, the first electrical pulse emitter 120, the first electrical pulse sampler 150 and the database 172. The computer 170 determines a time delay between the electrical pulse emission into the first probe 30A and receipt of the sensed electrical pulse reflection from the first probe 30A.

The computer 170 is also electronically coupled with the second probe 30B, the second electrical pulse emitter 120, the second electrical pulse sampler 150 and the database 172. The computer 170 also determines a time delay between the electrical pulse emission into the second probe 30B and receipt of the sensed electrical pulse reflection from the second probe 30B.

The computer 170 performs the time domain evaluation by correlating and comparing the determined time delay between pulse emission and pulse reflection receipt to the information within the database 172 to match the determined time delay to similar time delays generated by known dielectric constants, and then the computer 170 correlates the identified dielectric constant to known and previously determined volume fraction constituents 15, 16, 17 having such dielectric constants. The computer also performs the frequency domain evaluation by determining/calculating the resonance points of the volume fraction constituents 15, 16, 17 and concentrations thereof in the fluid 14 by applying a Fast Fourier Transform (FFT) to the previously determined time delay. A Power Spectral Density (PSD) evaluation is then made of the calculated resonance points by the computer 170 to determine the average power, amplitude and frequency of the volume fraction constituents 15, 16, 17. The computer 170 then correlates the resonance points resulting from the FFT and PSD to the previously calculated and known resonance points as provided in the database 172 as a second measure to identify the volume fraction constituents 15, 16, 17 in the fluid 14 and to measure the volume of the volume fraction constituents 15, 16, 17 in the fluid 14.

A first output (not shown) is generated by the first probe 30A when a volume fraction constituent 15, 16, 17 is sensed by the first probe 30A, and a second output (not shown) is generated by the second probe 30B when the same volume fraction constituent 15, 16, 17 is subsequently sensed by the second probe 30B. The first and second probe outputs (not shown) are communicated to the computer 170 through the coaxial cable 75 wherein the computer 170 uses the time delay between the first probe 30A output and the second probe 30B output to determine the velocity of the volume fraction constituents 15, 16, 17 moving through the pipe 20.

The user interface 210 is electronically coupled with the computer 170 and receives the identification of the volume fraction constituents 15, 16, 17 and the volume fraction 15, 16, 17 volume calculation data from the computer 170 to generate a user perceivable output (not shown) which identifies the volume fraction constituents 15, 16, 17 in the fluid 14 and the volume thereof moving through the pipe 20 continuously and in real time.

The instant invention also provides a method for identifying and measuring the volume fraction constituents 15, 16, 17 of a fluid 14. The method is first initiated by providing a source of fluid 13 which communicates with the pipe 20 that defines a medial channel 28 for the fluid 14 to move therethrough. The fluid 14 has a volume fraction constituent 15, 16, 17 and each volume fraction constituent 15, 16, 17 has a previously calculated and known dielectric constant and previously calculated and known resonance points.

The database 172, which is assessable by the computer 170, has stored assessable information about the previously calculated and known dielectric constant of each volume fraction constituent 15, 16, 17 and stored assessable information about the previously calculated and known resonance points of each volume fraction constituent 15, 16, 17, and each volume fraction constituent at various concentrations.

The first probe 30A is positionally maintained within the upstream grayloc support 80, and the first probe 30A is exposed, at least in part, to the fluid 14 moving through the medial channel 28 of the pipe 20 and through the upstream grayloc support 80. The second probe 30B is similarly positionally maintained within a second grayloc support 80A, and the second probe 30B is exposed, at least in part, to the fluid 14 moving through the medial channel 28 of the pipe 20 and through the second grayloc support 80A downstream a known distance 76 from the first probe 30A.

The back pressure regulator 110 which communicates with the medial channel 28 of the pipe 20 maintains fluid pressure within the medical channel 28 and about the first and second probes 30A, 30B respectively, at a pressure at least equal to the pressure of the source of fluid 13 to prevent boiling of the fluid 14 within the medial channel 28 of the pipe 20.

The first electrical pulse emitter 120 electronically generates an electrical pulse that is conveyed to the first probe 30A through the coaxial cable 75. The electrical pulse is conveyed into the first probe 30A and generates an electrical pulse reflection when the electrical pulse travels the entire active length of the first probe 30A, or earlier interacts with a changed electrical impedance or a changed dielectric constant of a volume fraction constituent 15, 16, 17 to which the first probe 30A is at least partially exposed. The pulse reflection is received by the first electrical pulse sampler 150 that is electronically coupled with the first probe 30A by the coaxial cable 75.

Similarly, the second electrical pulse emitter 120 electronically generates an electrical pulse that is conveyed to the second probe 30B through the coaxial cable 75. The electrical pulse is conveyed into the second probe 30B and a generates an electrical pulse reflection when the electrical pulse travels the entire active length of the second probe 30B or earlier interacts with a changed electrical impedance or a changed dielectric constant of a volume fraction constituent 15, 16, 17 to which the second probe 30B is at least partially exposed. The pulse reflection is received by a second electrical pulse sampler 150 that is electronically coupled with the second probe 30B by the coaxial cable 75.

The computer 170 is electronically coupled with the probes 30A, 30B the electrical pulse emitters 120, the electrical pulse samplers 150 and the database 172.

The computer 170 determines a time delay between the electrical pulse emission into each probe 30A, 30B and receipt of the electrical pulse reflections from each probe 30A, 30B.

The computer 170 correlates the determined time delay between the electrical pulse emission into each probe 30A, 30B, and receipt of the electrical pulse reflection from the respective probe 30A, 30B to the information stored within the database 172 of known time delays generated by known dielectric constants of known volume fraction constituents 15, 16, 17 to provide a measure to identify the volume fraction constituents 15, 16, 17 within the fluid 14.

The computer 170 also applies a Fast Fourier Transform (FFT) to the determined time delay to generate a sine wave frequency based upon the determined time delay. The computer 170 also calculates the Power Spectral Density (PSD) of the generated sine wave frequency to determine the average power, amplitude and frequency of the sine wave to identify resonance points. The computer 170 correlates the frequency from the Fast Fourier Transform (FFT) and the resonance points of the PSD to the database 172 of known resonance points of known volume fraction constituents 15, 16, 17 to provide another measure to identify the volume fraction constituents 15, 16, 17 within the fluid 14 and also to measure the volume of the volume fraction constituents 15, 16, 17 in the fluid 14.

A first output (not shown) is generated by the first probe 30A when a volume fraction constituent 15, 16, 17 is sensed by the first probe 30A and identified by the computer 170, and a second output (not shown) is generated by the second probe 30B when the same volume fraction constituent 15, 16, 17 is subsequently sensed by the second probe 30B and identified by the computer 170.

The volume of each volume fraction constituent 15, 16, 17 moving through the pipe 20 is calculated by using the determined time delay between the first probe 30A output and the second probe 30B output by calculating the velocity of the sensed volume fraction constituent 15, 16, 17 moving the known distance 76 and using the known interior diameter 23 of the pipe 20.

The user interface 210 which is electronically coupled with the computer 170 and which receives the identification of the volume fraction constituent 15, 16, 17, and the first probe 30A output (not shown) and the second probe 30B output (not shown) and the correlation of resonance points of the volume fraction constituents 15, 16, 17 generates a user perceivable output (not shown) which identifies each volume fraction constituent 15, 16, 17 in the fluid 14, and the volume thereof moving through the pipe 20 on a real-time and continuous basis.

We claim:

1. An apparatus for identifying and measuring a volume fraction constituent of a fluid, comprising:

a source of fluid with a known temperature, and having a volume fraction constituent, and wherein the volume fraction constituent has a previously calculated, and known dielectric constant and previously calculated and known resonance points, and wherein information about the previously calculated, and known dielectric constant and previously calculated and known resonance points of the volume fraction constituent is stored in, and is accessible from a database;

a probe exposed, at least in part, to the fluid, and wherein the probe has a known length;

an electrical pulse emitter which electronically generates a predetermined electrical pulse which is delivered to the probe, and which further travels the known length of the probe and which generates an electrical pulse reflection;

an electrical pulse sampler which electronically communicates with the probe and which further receives and senses the electrical pulse reflection generated by the electrical pulse within the probe;

a computer electrically coupled with the probe, electrical pulse emitter, electrical pulse sampler and the database, and wherein the computer determines a time period between the electrical pulse emission into the probe, and receipt of the sensed electrical pulse reflection, and wherein resonance points of the volume fraction constituent are calculated by the computer from the determined time period, and wherein the computer further correlates the determined time period to the previously calculated, and known dielectric constant and the previously calculated and known resonance points of the volume fraction constituent as provided in the database so as to identify the volume fraction constituent in the fluid; and a user interface electrically coupled with the computer, and which further generates a user perceivable output which identifies the volume fraction constituent.

2. The apparatus of claim 1 wherein the volume fraction constituent is selected from the group consisting of petroleum, oil, water, natural gas, drilling fluid, drilling fluid components and particulated solids.

3. The apparatus of claim 1 wherein the volume fraction constituent is a multiplicity of volume fraction constituents.

4. The apparatus of claim 3 wherein the multiplicity of volume fraction constituents includes a fluid and a gas.

5. The apparatus of claim 1 further comprising:
a pipe having a known interior diameter communicating with the source of the fluid so that a volume of the fluid moves through the pipe;
a second probe exposed at least in part to the fluid moving through the pipe a known distance downstream from the first probe;
a first output generated by the first probe when a volume fraction constituent is sensed by the first probe and a second output generated by the second probe when the same volume fraction constituent is sensed by the second probe, and wherein the first and second probe outputs are communicated to the computer; and
the computer determines a time difference between the first probe output and the second probe output and uses the determined time difference between the first probe output and the second probe output to determine the velocity of the volume fraction constituent moving through the pipe and by correlating the determined velocity with a known total volume of fluid moving through the pipe a volume of the volume fraction constituent by unit of time is determined.

6. The apparatus of claim 5 further comprising:
a backpressure regulator communicating with the pipe to maintain fluid pressure within the pipe and about the probes at a pressure at least equal to the pressure of the source of the fluid to prevent boiling of the fluid within the pipe.

7. The apparatus of claim 1 further comprising:
a backpressure regulator communicating with the pipe to maintain fluid pressure within the pipe and about the probes at a pressure at least equal to the pressure of the source of the fluid to prevent boiling of the fluid within the pipe.

8. An apparatus for identifying and measuring a volume fraction constituent of a fluid, comprising:
a source of fluid communicating with a pipe defining a medial channel to provide fluid moving therethrough at a velocity, the fluid having a volume fraction constituent and wherein the volume fraction constituent has a previously calculated and known dielectric constant and previously calculated and known resonance points and wherein information about the previously calculated, and known dielectric constant and previously calculated and known resonance points of the volume fraction constituent is stored in and is accessible from a database;
a first probe exposed at least in part to the fluid moving through the pipe, the first probe having a known length;
a second probe exposed at least in part to the fluid moving through the pipe a known distance downstream of the first probe, the second probe having a known length;
a backpressure regulator communicating with the medial channel defined by the pipe to maintain fluid pressure about the first and second probes at a pressure at least equal to the pressure of the source of the fluid to prevent boiling of the fluid within the medial channel;
an electrical pulse emitter which electronically generates a predetermined electrical pulse which is delivered to the first probe, and the pulse travels along and through the first probe and generates an electrical pulse reflection;
an electrical pulse sampler which electronically communicates with the first probe and which further receives and senses the electrical pulse reflection generated by electrical pulse within the first probe;
an electrical pulse emitter which electronically generates a predetermined electrical pulse which is delivered to the second probe, and the pulse travels along and through the second probe and generates an electrical pulse reflection;
an electrical pulse sampler which electronically communicates with the second probe and which further receives and senses the electrical pulse reflection generated by electrical pulse within the second probe;
a computer electrically coupled with the first probe, the electrical pulse emitter, the electrical pulse sampler, and the database, and wherein the computer determines a time period between the electrical pulse emission into the first probe, and the receipt of the sensed electrical pulse reflection from the first probe, and wherein resonance points of the volume fraction constituent are calculated by the computer from the determined time period, and wherein the computer further correlates the determined time period to the previously calculated, and known dielectric constant and the previously calculated and known resonance points of the volume fraction constituent as provided in the database so as to identify the volume fraction constituent in the fluid;
a computer electrically coupled with the second probe, the electrical pulse emitter, the electrical pulse sampler, and the database, and wherein the computer determines a time period between the electrical pulse emission into the second probe, and the receipt of the sensed electrical pulse reflection from the second probe, and wherein the resonance points of the volume fraction constituent are calculated by the computer from the determined time period, and wherein the computer further correlates the determined time period to the previously calculated, and known dielectric constant and the previously calculated and known resonance points of the volume fraction constituent as provided in the database so as to identify the volume fraction constituent in the fluid;
a first output generated by the first probe when a volume fraction constituent is sensed by the first probe, and a second output generated by the second probe when the same volume fraction constituent is sensed by the second probe, and wherein the first and second probe outputs are communicated to the computer;

the computer determines a time difference between the first probe output and the second probe output and uses the determined time difference between the first probe output and the second probe output to determine the velocity of the volume fraction constituent within the medial channel defined by the pipe and by correlating the determined velocity with a known total volume of fluid moving through the pipe a volume of the volume fraction constituent by amount of time is determined; and a user interface electrically coupled with the computer and which receives the identification of the volume fraction constituent and the first probe output and the second probe output, and which further generates a user perceivable output which identifies the volume fraction constituent in the fluid and the volume of the volume fraction constituent moving through the pipe.

* * * * *